United States Patent
Saito

(10) Patent No.: US 9,629,555 B2
(45) Date of Patent: Apr. 25, 2017

(54) ENDOSCOPE SYSTEM, ENDOSCOPE SYSTEM PROCESSOR DEVICE, OPERATION METHOD FOR ENDOSCOPE SYSTEM, AND OPERATION METHOD FOR ENDOSCOPE SYSTEM PROCESSOR DEVICE

(71) Applicant: FUJIFILM Corporation, Tokyo (JP)

(72) Inventor: Takaaki Saito, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 262 days.

(21) Appl. No.: 14/611,337

(22) Filed: Feb. 2, 2015

(65) Prior Publication Data
US 2015/0238086 A1 Aug. 27, 2015

(30) Foreign Application Priority Data

Feb. 27, 2014 (JP) ................. 2014-037595

(51) Int. Cl.
- *A61B 5/1455* (2006.01)
- *A61B 1/06* (2006.01)
- *A61B 5/00* (2006.01)
- *A61B 1/00* (2006.01)

(52) U.S. Cl.
CPC ........ *A61B 5/0075* (2013.01); *A61B 1/00006* (2013.01); *A61B 1/00009* (2013.01); *A61B 1/06* (2013.01); *A61B 1/0638* (2013.01); *A61B 5/0084* (2013.01); *A61B 5/14551* (2013.01); *A61B 1/0646* (2013.01); *A61B 1/0653* (2013.01); *A61B 2576/00* (2013.01)

(58) Field of Classification Search
CPC .............. A61B 5/1455; A61B 5/14551; A61B 5/14552; A61B 5/0075; A61B 1/0009; A61B 1/06; A61B 5/7264; A61B 5/7271
See application file for complete search history.

(56) References Cited

U.S. PATENT DOCUMENTS

| | | | | |
|---|---|---|---|---|
| 5,956,416 | A * | 9/1999 | Tsuruoka | A61B 1/00009 348/65 |
| 8,834,359 | B2 * | 9/2014 | Ozawa | A61B 1/0638 600/109 |
| 2012/0116192 | A1 | 5/2012 | Saito | |
| 2012/0179013 | A1 | 7/2012 | Saito | |

FOREIGN PATENT DOCUMENTS

| JP | 5231511 B2 | 7/2013 |
|---|---|---|
| JP | 5302984 B2 | 10/2013 |

* cited by examiner

*Primary Examiner* — Eric Winakur
(74) *Attorney, Agent, or Firm* — Birch, Stewart, Kolasch & Birch, LLP

(57) ABSTRACT

An exposure amount designation value calculation unit calculates an exposure amount designation value for designating the amount of exposure, which is required to image an observation target, based on an image signal. A threshold value calculation unit calculates a threshold value for comparison with the pixel value of the image signal according to the exposure amount designation value. A region detection unit detects a first region, in which the pixel value falls within a range set by the threshold value, and a second region, in which the pixel value is out of the range. An image generation unit generates an oxygen saturation image, in which the oxygen saturation is displayed differently in the first and second regions, using the image signal, the oxygen saturation, and information of the first and second regions.

18 Claims, 20 Drawing Sheets

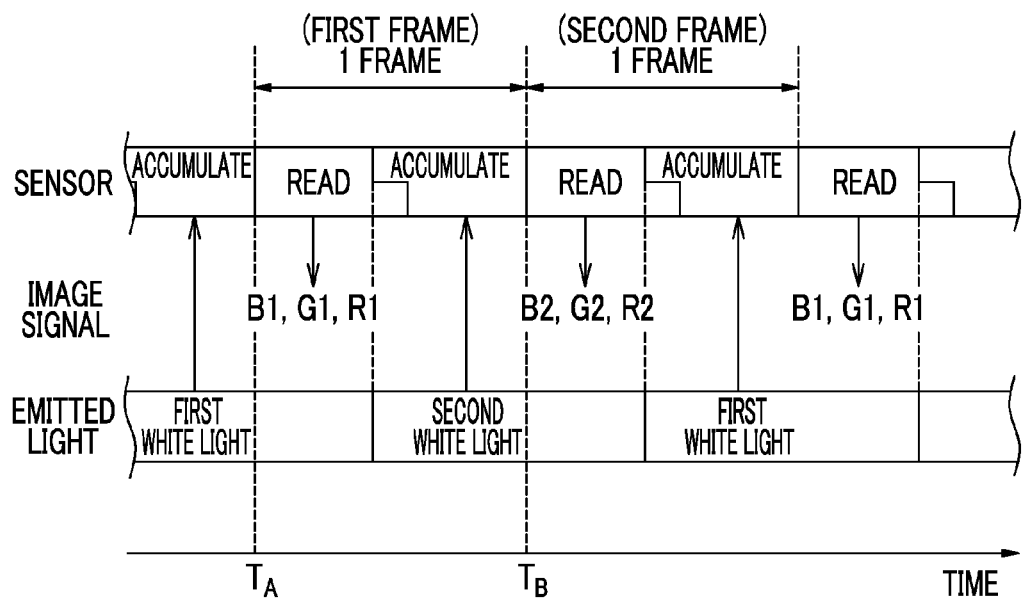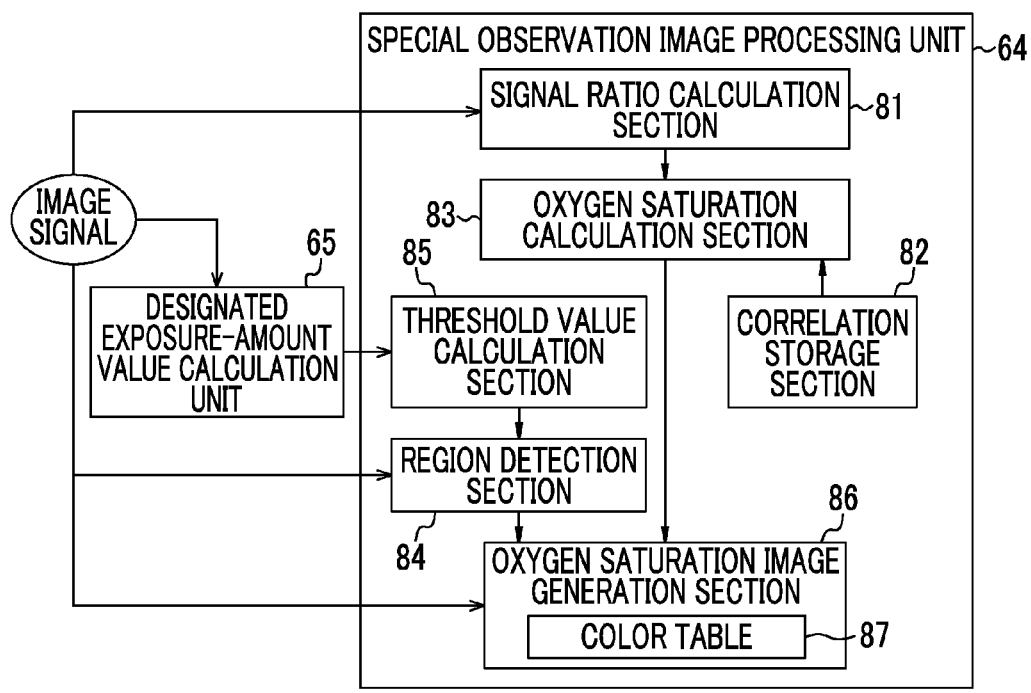

FIG. 13A
FIG. 13B
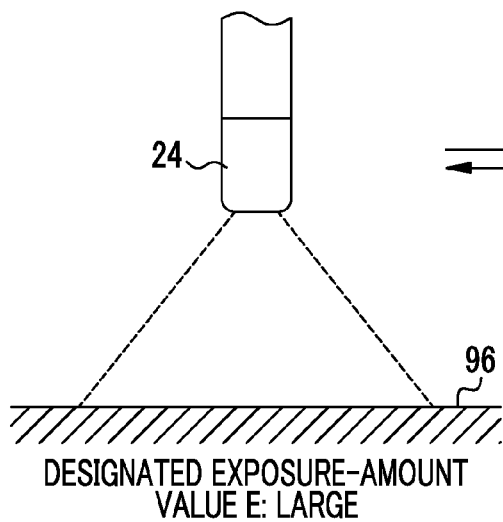
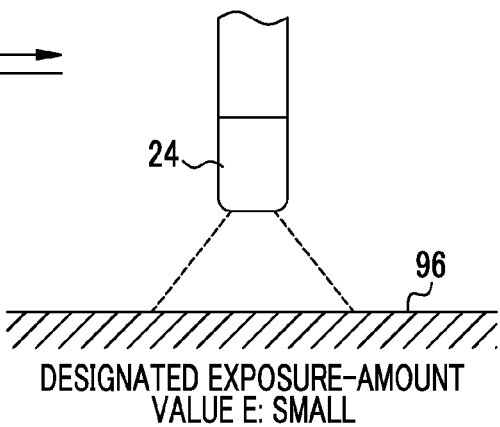
FIG. 14
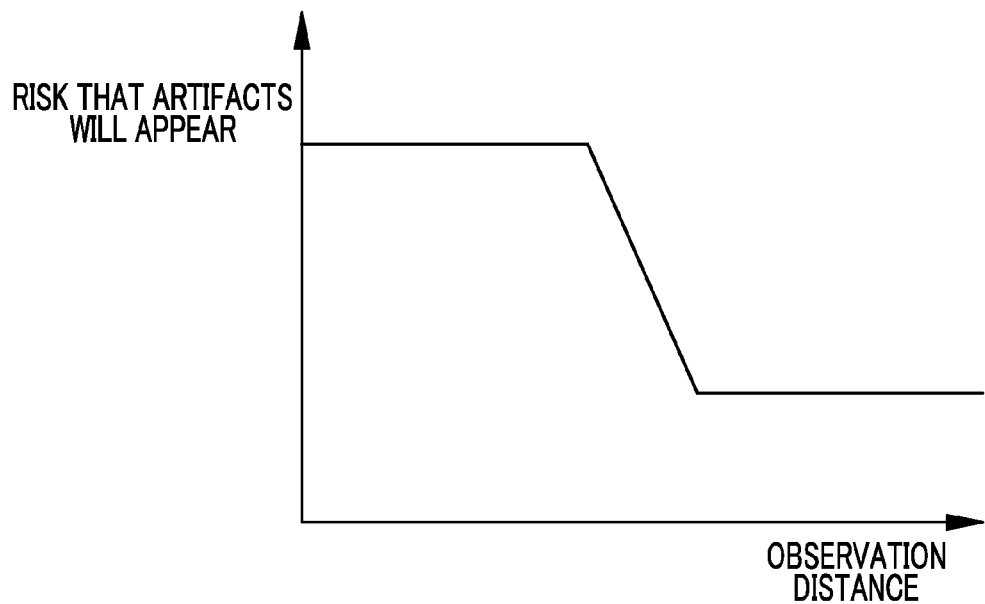

ENDOSCOPE SYSTEM, ENDOSCOPE SYSTEM PROCESSOR DEVICE, OPERATION METHOD FOR ENDOSCOPE SYSTEM, AND OPERATION METHOD FOR ENDOSCOPE SYSTEM PROCESSOR DEVICE

CROSS-REFERENCE TO RELATED APPLICATIONS

The present application claims priority under 35 U.S.C. §119 to Japanese Patent Application No. 2014-037595, filed on Feb. 27, 2014, all of which are hereby expressly incorporated by reference into the present application.

BACKGROUND OF THE INVENTION

1. Field of the Invention

The present invention relates to an endoscope system, an endoscope system processor device, an operation method for an endoscope system, and an operation method for an endoscope system processor device for calculating biological function information regarding the oxygen saturation of blood hemoglobin from an image signal obtained by imaging an observation target in a subject.

2. Description of the Related Art

In the medical field, it is common to perform diagnosis using an endoscope system including a light source device, an endoscope, and a processor device. In recent years, diagnosis of a lesion using the oxygen saturation of blood hemoglobin among pieces of biological function information has been performed. As a method of acquiring the oxygen saturation, a method is known in which first signal light and second signal light having different wavelength bands and different absorption coefficients for oxygenated hemoglobin and reduced hemoglobin are alternately emitted to the observation target and reflected light beams of the first and second signal light beams are detected by a sensor located at the distal end of the endoscope (refer to JP5302984B and JP5231511B). The ratio of signal values (hereinafter, referred to as a signal ratio) of pixels of an image signal corresponding to the reflected light of the first signal light detected by the sensor and an image signal corresponding to the reflected light of the second signal light detected by the sensor is maintained as a fixed value if there is no change in the oxygen saturation in the blood vessel. However, if there is a change in the oxygen saturation, the signal ratio is also changed accordingly. Therefore, it is possible to calculate the oxygen saturation based on the signal ratio of the image signals.

However, when the signal ratio changes due to factors other than blood hemoglobin, such as when there is dirt on the mucous membrane surface (for example, attachment of residue or opaque mucus), when artifacts appear, or when dye for coloring is used, the oxygen saturation calculation accuracy may be lowered. In the technique disclosed in JP5302984B, not only the value of the oxygen saturation but also the calculation accuracy is displayed by generating and displaying an oxygen saturation image in which the tone of pseudo color showing the oxygen saturation changes according to the calculation accuracy. More specifically, the "reliability" of the oxygen saturation is calculated based on the pixel value of the image signal, and the magnitude of the oxygen saturation is displayed by the pseudo color of blue to red in a high-reliability pixel, while the magnitude of the oxygen saturation is displayed by monochrome tone in a low-reliability pixel.

SUMMARY OF THE INVENTION

If there is a factor that changes the signal ratio other than the blood hemoglobin, the oxygen saturation calculation accuracy may be lowered as described above. However, even under the conditions in which it can be regarded that most factors that change the signal ratio are the blood hemoglobin, the oxygen saturation calculation accuracy may be lowered. Specifically, even if there is no dirt on the mucous membrane, the error of the oxygen saturation may be increased when the distal end of the endoscope is brought close to the observation target. Such noise of an image caused by unnatural error or the like occurring due to technical problems of the endoscope system regardless of the properties of the observation target is referred to as artifacts.

For example, when the pixel of an imaging device is saturated by the reflected light beams of the first and second signal light beams by bringing the distal end of the endoscope close to the observation target, it is not possible to accurately calculate the oxygen saturation. In this case, the endoscope system adjusts the amount of exposure automatically so that the pixel of the imaging device is not saturated. Accordingly, it is possible to observe the observation target with the same brightness and color at all times. However, even if there is no dirt on the mucous membrane, no use of dye, and no appearance of artifacts and automatic exposure adjustment is performed so that the observation target can be appropriately observed, error may occur in the oxygen saturation if the distal end of the endoscope is brought close to the observation target. This error may appear as artifacts in the oxygen saturation image showing the oxygen saturation.

It is an object of the invention to provide an endoscope system, an endoscope system processor device, an operation method for an endoscope system, and an operation method for an endoscope system processor device for calculating the oxygen saturation and for acquiring information regarding a region where error occurs in the oxygen saturation and appears as artifacts in an oxygen saturation image.

An endoscope system of the invention includes an illumination unit, an image signal acquisition unit, an oxygen saturation calculation unit, an exposure amount designation value calculation unit, a threshold value calculation unit, a region detection unit, and an image generation unit. The illumination unit generates illumination light to irradiate an observation target. The image signal acquisition unit includes an imaging device that images the observation target with reflected light of the illumination light, and acquires a plurality of image signals from the imaging device, the plurality of image signals corresponding to a plurality of wavelength ranges including a wavelength range where an absorption coefficient changes according to oxygen saturation of blood hemoglobin. The oxygen saturation calculation unit calculates the oxygen saturation based on the image signals. The exposure amount designation value calculation unit calculates an exposure amount designation value for designating an amount of exposure, which is required to image the observation target, based on the image signals. The threshold value calculation unit calculates a threshold value for comparison with pixel values of the image signals according to the exposure amount designation value. The region detection unit detects a first region, in which the pixel values fall within a range set by the threshold value, and a second region, in which the pixel values are out of the range. The image generation unit generates an oxygen saturation image, in which the oxygen saturation is displayed differently in the first and second regions, using the image signals, the oxygen saturation, and information of the first and second regions.

The threshold value calculation unit increases the threshold value as the exposure amount designation value increases. For example, the threshold value is one of a first threshold value used when the exposure amount designation value is greater than a first specific value, a second threshold value that is used when the exposure amount designation value is less than a second specific value set to be equal to or less than the first specific value and that is smaller than the first threshold value, and an intermediate value between the first and second threshold values that is used when the exposure amount designation value is equal to or greater than the second specific value and equal to or less than the first specific value. The intermediate value is a value that changes linearly with respect to the exposure amount designation value between the first and second threshold values.

For example, the image generation unit generates the oxygen saturation image in which one of the first and second regions is displayed in a color corresponding to a value of the oxygen saturation and the other region is displayed in a specific color that does not depend on the value of the oxygen saturation. In this case, for example, the image generation unit displays the specific color by setting a color difference signal to zero in the generated oxygen saturation image.

In addition, an endoscope system of the invention includes an illumination unit, an image signal acquisition unit, an oxygen saturation calculation unit, an exposure amount designation value calculation unit, a threshold value calculation unit, a region detection unit, and an image generation unit. The illumination unit generates illumination light to irradiate an observation target. The image signal acquisition unit includes an imaging device that images the observation target with reflected light of the illumination light, and acquires a plurality of image signals from the imaging device, the plurality of image signals corresponding to a plurality of wavelength ranges including a wavelength range where an absorption coefficient changes according to oxygen saturation of blood hemoglobin. The oxygen saturation calculation unit calculates the oxygen saturation based on the image signals. The exposure amount designation value calculation unit calculates an exposure amount designation value for designating an amount of exposure, which is required to image the observation target, based on the image signals. The threshold value calculation unit calculates a threshold value for comparison with a calculation value, which is calculated based on pixel values of the image signals, according to the exposure amount designation value. The region detection unit calculates the calculation value based on the image signals and detects a first region, in which the calculation value falls within a range set by the threshold value, and a second region, in which the pixel values are out of the range. The image generation unit generates an oxygen saturation image, in which the oxygen saturation is displayed differently in the first and second regions, using the image signals, the oxygen saturation, and information of the first and second regions.

The calculation value is, for example, a ratio of a pixel value of each pixel to an average value of pixel values of all pixels of the image signals. The calculation value may be an average value of pixel values.

A processor device for an endoscope system of the invention is a processor device for an endoscope system which includes an illumination unit configured to generate illumination light to irradiate an observation target and an imaging device configured to image the observation target with reflected light of the illumination light and in which a plurality of image signals corresponding to a plurality of wavelength ranges including a wavelength range where an absorption coefficient changes according to oxygen saturation of blood hemoglobin are output from the imaging device, and includes an image signal acquisition unit, an oxygen saturation calculation unit, an exposure amount designation value calculation unit, a threshold value calculation unit, a region detection unit, and an image generation unit. The image signal acquisition unit acquires the image signals. The oxygen saturation calculation unit calculates the oxygen saturation based on the image signals. The exposure amount designation value calculation unit calculates an exposure amount designation value for designating an amount of exposure, which is required to image the observation target, based on the image signals. The threshold value calculation unit calculates a threshold value for comparison with pixel values of the image signals according to the exposure amount designation value. The region detection unit detects a first region, in which the pixel values fall within a range set by the threshold value, and a second region, in which the pixel values are out of the range. The image generation unit generates an oxygen saturation image, in which the oxygen saturation is displayed differently in the first and second regions, using the image signals, the oxygen saturation, and information of the first and second regions.

An operation method for an endoscope system of the invention includes an illumination light generation step, an image signal acquisition step, an oxygen saturation calculation step, an exposure amount designation value calculation step, a threshold value calculation step, a region detection step, and an image generation step. In the illumination light generation step, an illumination unit generates illumination light to irradiate an observation target. In the image signal acquisition step, by imaging the observation target with reflected light of the illumination light using an imaging device, a plurality of image signals corresponding to a plurality of wavelength ranges including a wavelength range where an absorption coefficient changes according to oxygen saturation of blood hemoglobin are acquired from the imaging device. In the oxygen saturation calculation step, an oxygen saturation calculation unit calculates the oxygen saturation based on the image signals. In the exposure amount designation value calculation step, an exposure amount designation value calculation unit calculates an exposure amount designation value for designating an amount of exposure, which is required to image the observation target, based on the image signals. In the threshold value calculation step, a threshold value calculation unit calculates a threshold value for comparison with pixel values of the image signals according to the exposure amount designation value. In the region detection step, a region detection unit detects a first region, in which the pixel values fall within a range set by the threshold value, and a second region, in which the pixel values are out of the range. In the image generation step, an image generation unit generates an oxygen saturation image, in which the oxygen saturation is displayed differently in the first and second regions, using the image signals, the oxygen saturation, and information of the first and second regions.

An operation method for a processor device of the invention is an operation method for a processor device used in an endoscope system which includes an illumination unit configured to generate illumination light to irradiate an observation target and an imaging device configured to image the observation target with reflected light of the illumination light and in which a plurality of image signals corresponding to a plurality of wavelength ranges including a wavelength range where an absorption coefficient changes according to oxygen saturation of blood hemoglobin are output from the imaging device, and includes an image signal acquisition step, an oxygen saturation calculation step, an exposure amount designation value calculation step, a threshold value calculation step, a region detection step, and an image generation step. In the image signal acquisition step, image signals are acquired. In the oxygen saturation calculation step, an oxygen saturation calculation unit calculates the oxygen saturation based on the image signals. In the exposure amount designation value calculation step, the exposure amount designation value calculation unit calculates an exposure amount designation value for designating an amount of exposure, which is required to image the observation target, based on the image signals. In the threshold value calculation step, a threshold value calculation unit calculates a threshold value for comparison with pixel values of the image signals according to the exposure amount designation value. In the region detection step, a region detection unit detects a first region, in which the pixel values fall within a range set by the threshold value, and a second region, in which the pixel values are out of the range. In the image generation step, an image generation unit generates an oxygen saturation image, in which the oxygen saturation is displayed differently in the first and second regions, using the image signals, the oxygen saturation, and information of the first and second regions.

According to the endoscope system, the endoscope system processor device, the operation method for an endoscope system, and the operation method for an endoscope system processor device of the invention, it is possible to calculate the oxygen saturation and acquire information regarding a region where error occurs in the oxygen saturation and appears as artifacts in an oxygen saturation image.

BRIEF DESCRIPTION OF THE DRAWINGS

FIG. 7 is an explanatory diagram showing imaging control in the special observation mode.
FIG. 8 is a block diagram of a special observation image processing unit.
FIGS. 13A and 13B are explanatory diagrams showing the relationship between the observation distance and the exposure amount designation value.
FIG. 14 is a graph showing the relationship between the observation distance and the risk that error will occur in the oxygen saturation and appear as artifacts in the oxygen saturation image.

DESCRIPTION OF THE PREFERRED EMBODIMENTS

First Embodiment

Figure 1:
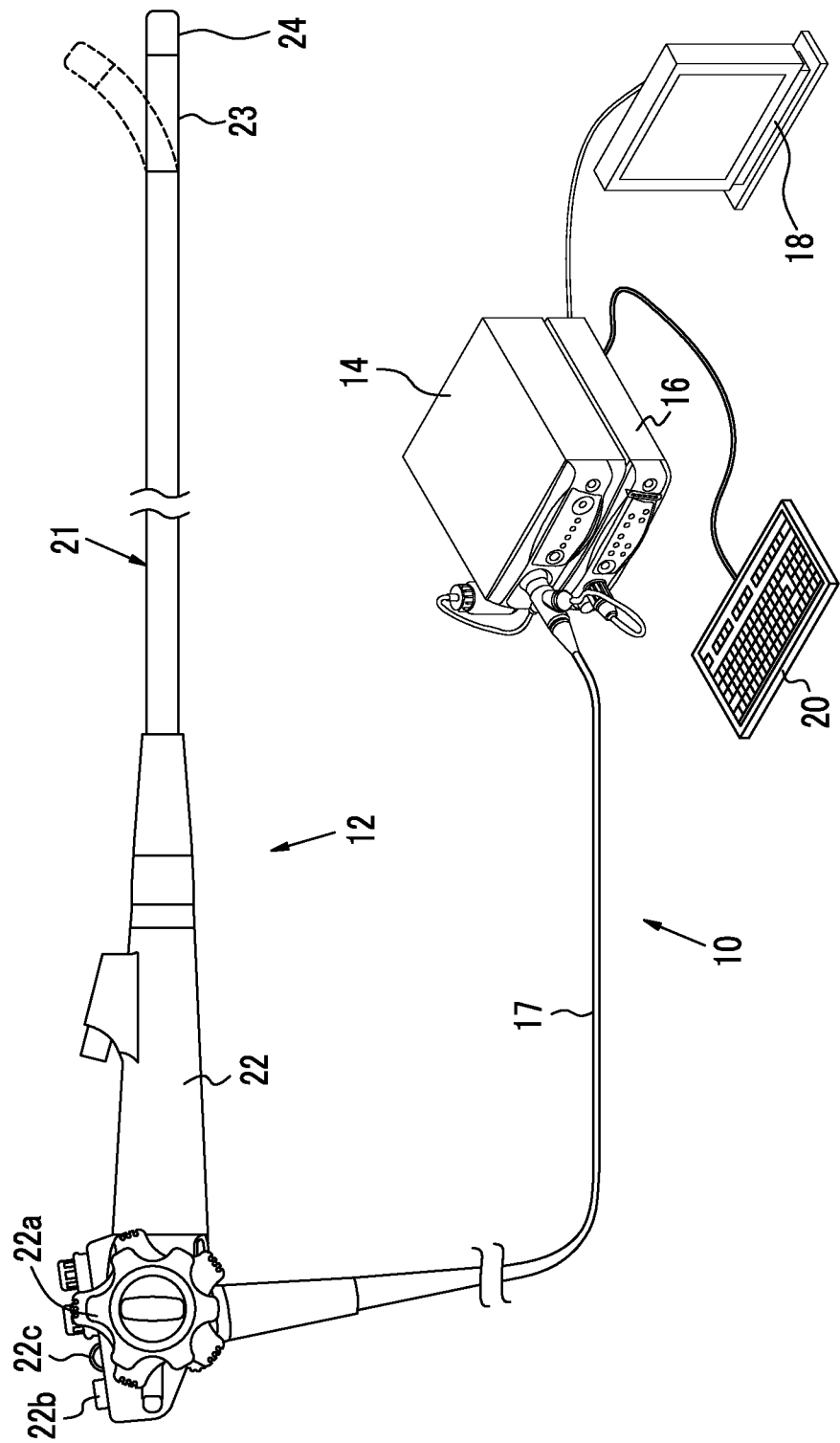
FIG. 1 is an external view of an endoscope system.

As shown in FIG. 1, an endoscope system 10 according to a first embodiment includes an endoscope 12, a light source device 14, a processor device 16, a monitor 18 (display unit), and a console 20. The endoscope 12 is optically connected to the light source device 14, and is electrically connected to the processor device 16. The endoscope 12 includes an insertion unit 21 that is inserted into a subject, an operating unit 22 provided at the base end of the insertion unit 21, and a bending portion 23 and a distal portion 24 that are provided at the distal side of the insertion unit 21. By operating an angle knob 22a of the operating unit 22, the bending portion 23 is bent. The distal portion 24 can be directed in a desired direction by the bending operation.

In addition to the angle knob 22a, an observation mode selector SW (observation mode selector switch) 22b, a zoom operation portion 22c, and a freeze button (not shown) for saving a still image are provided in the operating unit 22. The mode selector SW 22b is used for a switching operation between two modes of the normal observation mode and the special observation mode. The normal observation mode is a mode in which a normal light image obtained by full-color imaging of the observation target in the subject is displayed on the monitor 18. The special observation mode is a mode in which an oxygen saturation image obtained by imaging the oxygen saturation of blood hemoglobin of the observation target is displayed on the monitor 18. The zoom operation portion 22c is used for a zooming operation for driving a zoom lens 47 (refer to FIG. 2) in the endoscope 12 to magnify the observation target.

The processor device 16 is electrically connected to the monitor 18 and the console 20. The monitor 18 displays an image, such as a normal light image or an oxygen saturation image, and information regarding the image (hereinafter, referred to as image information or the like). The console 20 functions as a user interface (UI) for receiving an input operation, such as a function setting. A recording unit (not shown) in which image information or the like is recorded may be connected to the processor device 16.

Figure 2:
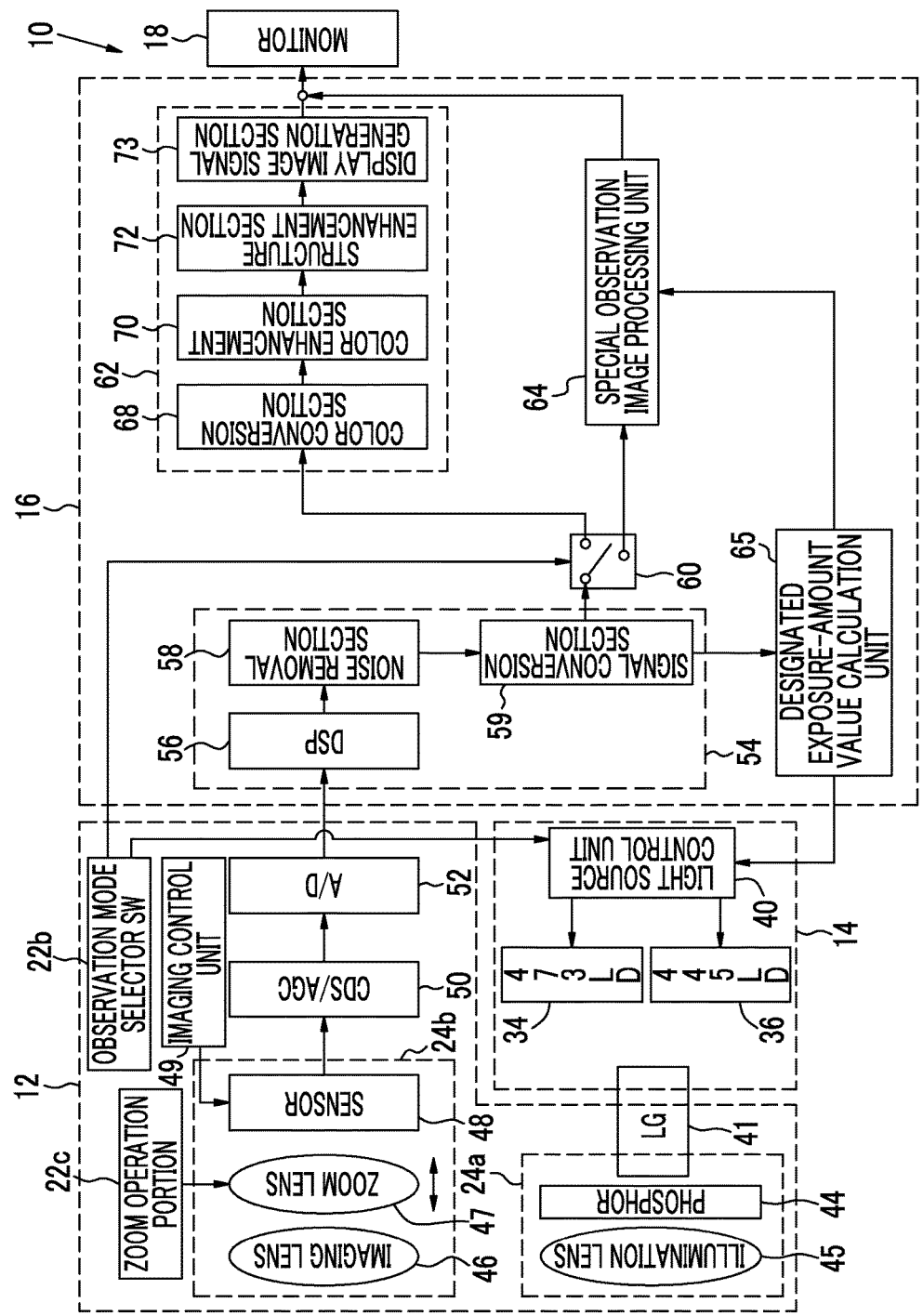
FIG. 2 is a block diagram of the endoscope system.

As shown in FIG. 2, the light source device 14 includes, as light emitting sources, a first blue laser light source (473 LD (laser diode)) 34 that emits first blue laser light having a center wavelength of 473 nm and a second blue laser light source (445 LD) 36 that emits second blue laser light having a center wavelength of 445 nm. The light emission amount and the light emission timing of each of the light sources 34 and 36 formed of the semiconductor light emitting elements are separately controlled by a light source control unit 40. For this reason, the light intensity ratio between light emitted from the first blue laser light source 34 and light emitted from the second blue laser light source 36 can be freely changed. The light source control unit 40 controls the amount of light emitted from each of the first and second blue laser light sources 34 and 36 based on the exposure amount designation value input from an exposure amount designation value calculation unit 65. Accordingly, the light source control unit 40 adjusts the amount of illumination light emitted to the observation target.

It is preferable that the half-width of each of the first and second blue laser light beams is set to about ±10 nm. As the first blue laser light source 34 and the second blue laser light source 36, a broad area type InGaN-based laser diode can be used, or an InGaNAs-based laser diode or a GaNAs-based laser diode can be used. As the light sources, it is possible to use a structure using a light emitter, such as a light emitting diode.

The light source control unit 40 turns on the second blue laser light source 36 in the normal observation mode. On the other hand, in the special observation mode, the light source control unit 40 turns on the first blue laser light source 34 and the second blue laser light source 36 alternately at intervals of one frame.

The first and second blue laser light beams emitted from the light sources 34 and 36 are incident on a light guide (LG) 41 through optical members, such as a condensing lens, an optical fiber, and a multiplexer (none are shown). The light guide 41 is built into a universal cord 17 that connects the endoscope 12 and the light source device 14 to each other (refer to FIG. 1) and the endoscope 12. The light guide 41 causes the first and second blue laser light beams to propagate from the light sources 34 and 36 to the distal portion 24 of the endoscope 12 therethrough. As the light guide 41, a multi-mode fiber can be used. As an example, it is possible to use a small-diameter fiber cable having a diameter of ϕ0.3 mm to ϕ0.5 mm that includes a core with a diameter of 105 µm, a cladding with a diameter of 125 µm, and a protective layer as an outer skin.

The distal portion 24 of the endoscope 12 includes an illumination optical system 24a and an imaging optical system 24b. A phosphor 44 and an illumination lens 45 are provided in the illumination optical system 24a. The first and second blue laser light beams are incident on the phosphor 44 from the light guide 41. The phosphor 44 emits fluorescence due to the first or second blue laser light emitted thereto. Some of the first or second blue laser light beams are transmitted through the phosphor 44. The light emitted from the phosphor 44 is emitted to the observation target through the illumination lens 45. The first blue laser light source 34, the second blue laser light source 36, and the phosphor 44 form an illumination unit that generates illumination light emitted to the observation target.

Figure 3:
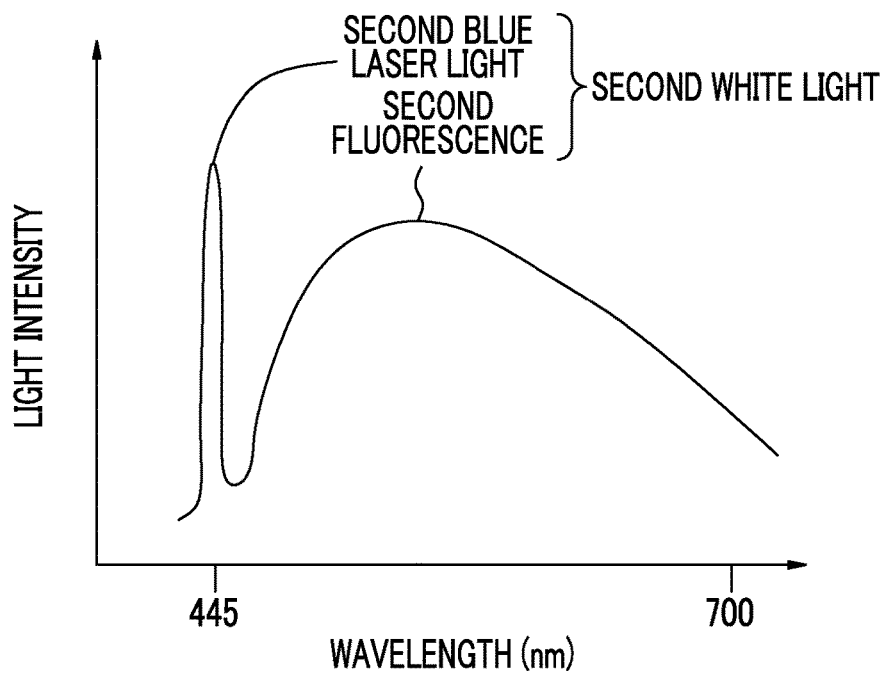
FIG. 3 is a graph showing the spectrum of light emitted in a normal observation mode.

In the normal observation mode, the second blue laser light is incident on the phosphor 44. Accordingly, white light having a spectrum shown in FIG. 3 (hereinafter, referred to as second white light) is emitted to the observation target as illumination light. The second white light is configured to include second blue laser light and second fluorescence of green to red that is excited and emitted from the phosphor 44 by the second blue laser light. Accordingly, the wavelength range of the second white light is the entire visible light region.

Figure 4:
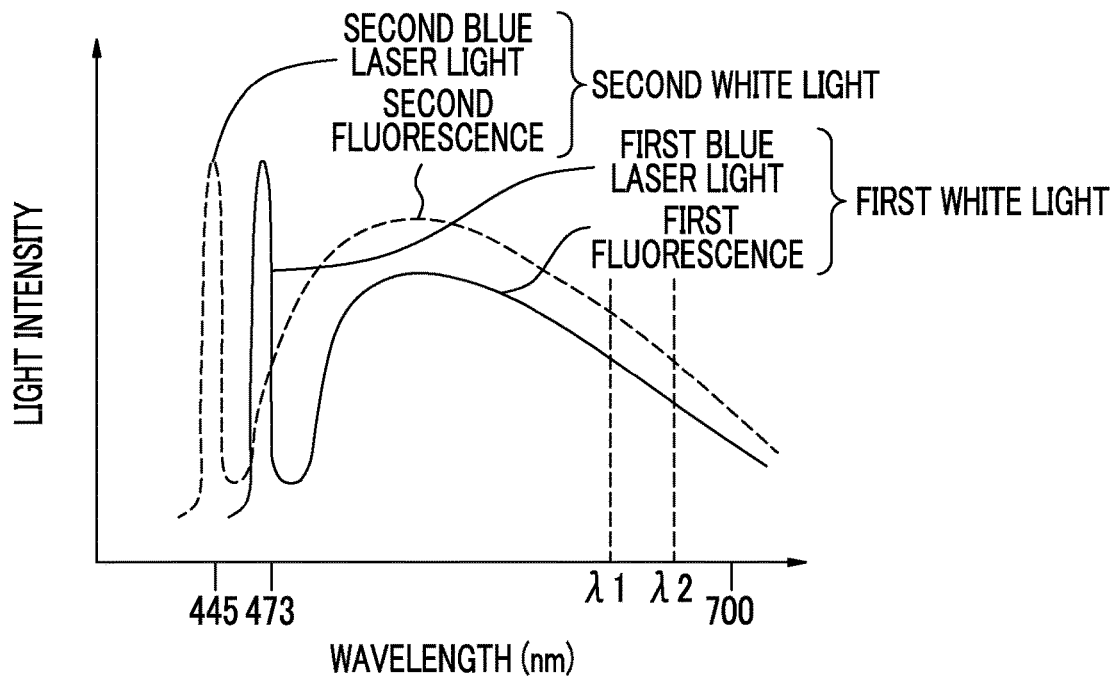
FIG. 4 is a graph showing the spectrum of light emitted in a special observation mode.

On the other hand, in the special observation mode, the first blue laser light and the second blue laser light are alternately incident on the phosphor 44. Therefore, as shown in FIG. 4, first white light and second white light having different emission spectrums are alternately emitted to the observation target as illumination light. The first white light is configured to include first blue laser light and first fluorescence of green to red that is excited and emitted from the phosphor 44 by the first blue laser light. Accordingly, the wavelength range of the first white light is the entire visible light region. The second white light is the same as the second white light emitted in the normal observation mode. In the present embodiment, the first white light is first illumination light, and the second white light is second illumination light.

The first fluorescence and the second fluorescence have almost the same waveform (shape of the spectrum), and the ratio between the intensity ($I1(\lambda)$) of the first fluorescence and the intensity ($I2(\lambda)$) of the second fluorescence (hereinafter, referred to as an inter-frame intensity ratio) is the same at any wavelength $\lambda$. For example, it is $I2(\lambda 1)/I1(\lambda 1)=I2(\lambda 2)/I1(\lambda 2)$. Since the inter-frame intensity ratio $I2(\lambda)/I1(\lambda)$ affects the calculation accuracy of the oxygen saturation, the inter-frame intensity ratio $I2(\lambda)/I1(\lambda)$ is accurately controlled by the light source control unit 40 such that the intensity ratio between reference frames set in advance is maintained.

As the phosphor 44, it is preferable to use a phosphor that absorbs some of the first and second blue laser light beams and includes a plurality of kinds of phosphors (for example, a YAG-based phosphor or a phosphor, such as BAM ($BaMgAl_{10}O_{17}$)) that are excited to emit green to red light beams. If a semiconductor light emitting element is used as a light source for exciting the phosphor 44 as in the present embodiment, it is possible to obtain high-intensity first and second white light beams with high luminous efficiency. In addition, it is possible to easily adjust the intensity of the white light and to suppress changes in color temperature and chromaticity.

The imaging optical system 24b of the endoscope 12 includes an imaging lens 46, the zoom lens 47, and a sensor 48 (refer to FIG. 2). Reflected light from the observation target is incident on the sensor 48 through the imaging lens 46 and the zoom lens 47. Then, a reflected image of the observation target is formed on the sensor 48. The zoom lens 47 is moved between the tele end and the wide end by operating the zoom operation portion 22c. When the zoom lens 47 is moved to the tele end side, the reflected image of the observation target is magnified. On the other hand, when the zoom lens 47 is moved to the wide end side, the reflected image of the observation target is reduced. When magnified observation is not performed (at the time of non-magnified observation), the zoom lens 47 is disposed at the wide end. When performing magnified observation, the zoom lens 47 is moved from the wide end to the tele end side by operating the zoom operation portion 22c.

The sensor 48 is a color imaging device, and captures a reflected image of the observation target and outputs the image signal. As the sensor 48, for example, a charge coupled device (CCD) image sensor or a complementary metal oxide semiconductor (CMOS) image sensor can be used. In the present embodiment, the sensor 48 is a CCD image sensor. The sensor 48 includes RGB pixels in which RGB color filters are provided on the imaging surface, and outputs image signals of three colors of R, and B by performing photoelectric conversion in pixels of respective colors of RGB.

Figure 5:
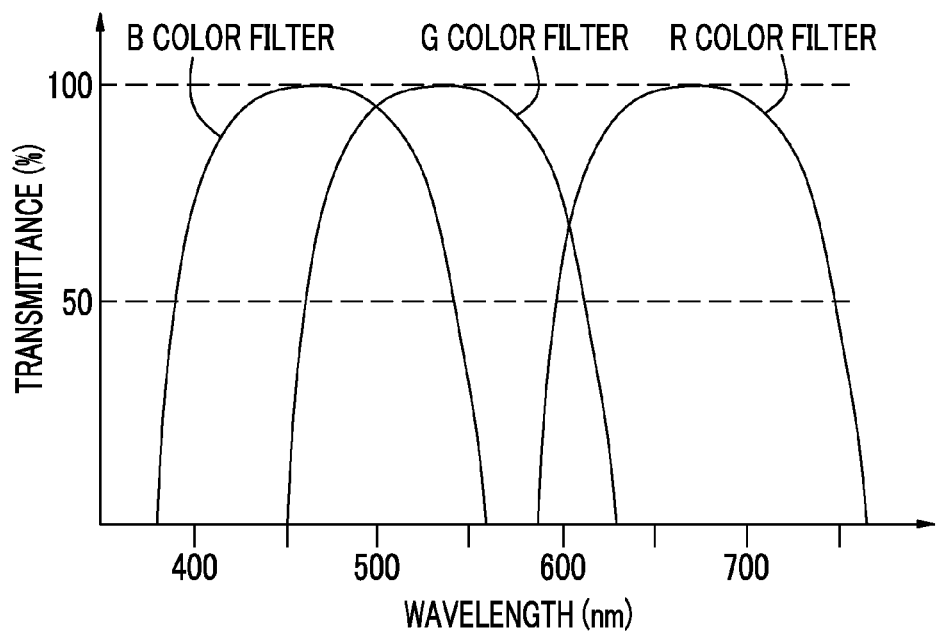
FIG. 5 is a graph showing the spectral transmittance of an RGB color filter.

As shown in FIG. 5, the B color filter has a spectral transmittance of 380 nm to 560 nm, the G color filter has a spectral transmittance of 450 nm to 630 nm, and the R color filter has a spectral transmittance of 580 nm to 760 nm. Accordingly, when the second white light is emitted to the observation target in the normal observation mode, the second blue laser light and some of green components of the second fluorescence are incident on the B pixel, some of green components of the second fluorescence are incident on the G pixel, and red components of the second fluorescence are incident on the R pixel. In the B image signal output from the B pixel, the emission intensity of the second blue laser light is significantly larger than that of the second fluorescence. Accordingly, most of the B image signal is occupied by the reflected light components of the second blue laser light.

On the other hand, when the first white light is emitted to the observation target in the special observation mode, the first blue laser light and some of green components of the first fluorescence are incident on the B pixel, some of green components of the first fluorescence and the first blue laser light attenuated by the G color filter are incident on the G pixel, and red components of the first fluorescence are incident on the R pixel. Since the emission intensity of the first blue laser light is significantly larger than that of the first fluorescence, most of the B image signal output from the B pixel is occupied by the reflected light components of the first blue laser light.

Light incidence components in the respective RGB pixels when the second white light is emitted to the observation target in the special observation mode are the same as those in the normal observation mode.

As the sensor 48, it is also possible to use a so-called complementary color image sensor including complementary color filters of C (cyan), M (magenta), Y (yellow), and G (green) on the imaging surface. When using the complementary color image sensor as the sensor 48, a color converter that performs color conversion from image signals of four colors of CMYG to image signals of three colors of RGB is preferably provided in the endoscope 12, the light source device 14, or the processor device 16. In this manner, even when complementary color image sensors are used, it is possible to obtain the image signals of three colors of RGB from the image signals of four colors of CMYG by color conversion.

Figure 6:
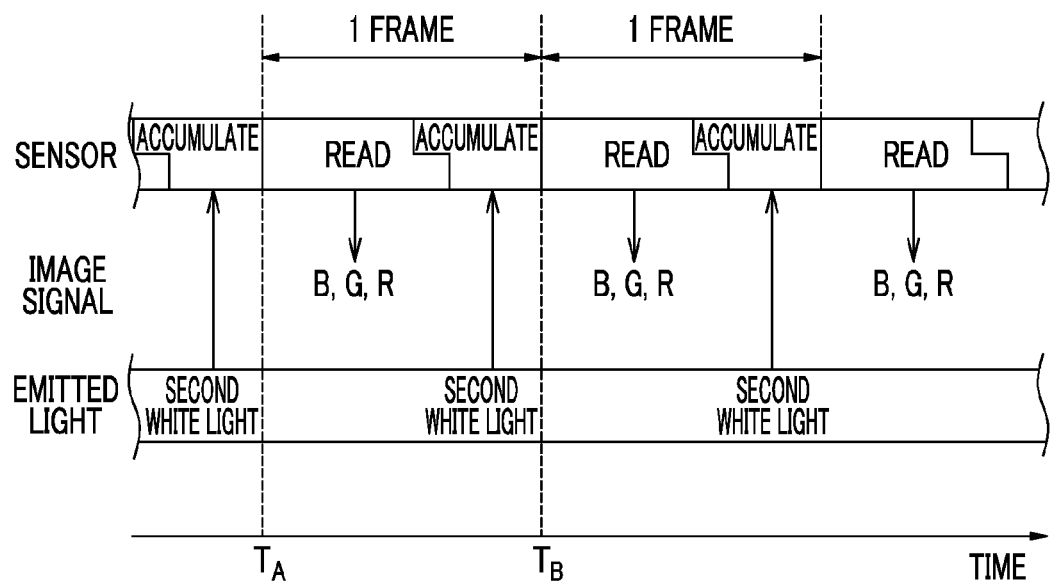
FIG. 6 is an explanatory diagram showing imaging control in the normal observation mode.

An imaging control unit 49 performs imaging control of the sensor 48. As shown in FIG. 6, in the normal observation mode, an observation target illuminated by the second white light is imaged by the sensor 48 for each period of one frame (hereinafter, simply referred to as one frame). Then, the image signals of RGB are output from the sensor 48 for each frame. In the present embodiment, the sensor 48 is a CCD image sensor. Accordingly, one frame is a period of the length from the end (time $T_A$) of a charge accumulation period (also referred to as an exposure period) to the end of the next charge accumulation period (time $T_B$), for example. In FIG. 6, one frame is divided into a reading period and a charge accumulation period. However, since the sensor 48 is a CCD image sensor, the approximately entire one frame can be set as a charge accumulation period, and signal charges accumulated in the previous frame can also be read during the accumulation of signal charges. The imaging control unit 49 also performs control, such as the adjustment of the length of the charge accumulation period.

Also in the special observation mode, the imaging control unit 49 performs imaging control of the sensor 48 in the same manner as in the normal observation mode. However, in the special observation mode, the first white light and the second white light are alternately emitted to the observation target in synchronization with the imaging frame of the sensor 48. Therefore, as shown in FIG. 7, the sensor 48 reads signal charges, which are obtained by imaging the observation target under the first white light, to the reading period of the first frame, and outputs the image signals of RGB colors. Then, the sensor 48 reads signal charges, which are obtained by imaging the observation target under the second white light, to the reading period of the second frame, and outputs the image signals of RGB colors. The sensor 48 outputs the image signals of RGB colors in both the first and second frames. However, the spectrum of white light in the first frame and the spectrum of white light in the second frame are different. Therefore, for the sake of distinction, the image signals of RGB colors that the sensor 48 outputs in the first frame are referred to as an R1 image signal, a G1 image signal, and a B1 image signal, and the image signals of RGB colors that the sensor 48 outputs in the second frame are referred to as an R2 image signal, a G2 image signal, and a B2 image signal.

In order to calculate the oxygen saturation, for example, a signal ratio B1/G2 between the B1 image signal and the G2 image signal and a signal ratio R2/G2 between the R2 image signal and the G2 image signal are used. Between these signal ratios, the signal ratio B1/G2 between the B1 image signal and the G2 image signal is a signal ratio that is required for the calculation of the oxygen saturation. For this reason, a component (first blue laser light transmitted through the phosphor 44) that becomes the B1 image signal in the first white light is the first signal light, and a component (green band component of the second fluorescence) that becomes the G2 image signal in the second white light is the second signal light.

The image signals of the respective colors output from the sensor 48 are transmitted to a correlated double sampling (CDS)/automatic gain control (AGC) circuit 50 (refer to FIG. 2). The CDS/AGC circuit 50 performs correlated double sampling (CDS) or automatic gain control (AGC) for the analog image signals output from the sensor 48. The image signals transmitted through the CDS/AGC circuit 50 are converted into digital image signals by an A/D converter 52. The image signals that have been digitized in this manner are input to the processor device 16.

The processor device 16 includes an image signal acquisition unit 54, an image processing switching unit 60, a normal observation image processing unit 62, a special observation image processing unit 64, and the exposure amount designation value calculation unit 65. The image signal acquisition unit 54 acquires an image signal from the sensor 48 of the endoscope 12. The image signal acquisition unit 54 includes a digital signal processor (DSP) 56, a noise removal section 58, and a signal conversion section 59.

The DSP 56 performs various kinds of signal processing, such as defect correction processing, offset processing, gain correction processing, linear matrix processing, gamma conversion processing, demosaic processing, and YC conversion processing, on the acquired image signal. In the defect correction processing, the signal of the defective pixel of the sensor 48 is corrected. In the offset processing, a dark current component is removed from the image signal subjected to the defect correction processing, and the exact zero level is set. In the gain correction processing, the signal level of each image signal is adjusted by multiplying each of the RGB image signals after the offset processing by a specific gain. Linear matrix processing for increasing color reproducibility is performed on the image signal of each color after the gain correction processing. Then, the brightness or saturation of each image signal is adjusted by gamma conversion processing. Demosaic processing (also referred to as isotropic processing or synchronization processing) is performed on the image signal after the linear matrix processing, and the signal of missing color of each pixel is generated by interpolation. Through the demosaic processing, all pixels have signals of RGB colors. The DSP 56 performs YC conversion processing on each image signal after the demosaic processing, and outputs a brightness signal Y and color difference signals Cb and Cr generated by the YC conversion processing to the noise removal section 58.

The noise removal section 58 performs noise removal processing using, for example, a moving average method or a median filter method on the image signal subjected to the demosaic processing or the like by the DSP 56. The image signals after noise has been removed are input to the signal conversion section 59, and are reconverted into RGB image signals. Then, the RGB image signals are input to the image processing switching unit 60 and the exposure amount designation value calculation unit 65.

The exposure amount designation value calculation unit 65 calculates an exposure amount designation value based on the image signals input from the signal conversion section 59. The exposure amount designation value is a control parameter for designating the amount of exposure for imaging the observation target. In order to calculate the exposure amount designation value, the exposure amount designation value calculation unit 65 calculates, for example, the average value of the brightness (hereinafter, referred to as an average brightness) of each pixel using the input image signals. When the average brightness is larger than a brightness determined by setting or the like (hereinafter, referred to as a set brightness), the exposure amount designation value calculation unit 65 calculates an exposure amount designation value to reduce the amount of exposure so that the average brightness becomes a value close to the set brightness. Conversely, when the average brightness is smaller than the set brightness, the exposure amount designation value calculation unit 65 calculates an exposure amount designation value to increase the amount of exposure so that the average brightness becomes a value close to the set brightness. When the average brightness is almost equal to the set brightness, the exposure amount designation value calculation unit 65 calculates an exposure amount designation value to designate the amount of exposure for maintaining the average brightness. Therefore, it is possible to image and observe the observation target with almost always the same brightness regardless of a change in the distance (observation distance) between the distal portion 24 and the observation target or a change in the relative direction (observation direction) between the distal portion 24 and the observation target.

The exposure amount designation value in the present embodiment is a control parameter that designates the amount of illumination light. Thus, the exposure amount designation value is input to the light source control unit 40, and the light source control unit 40 adjusts the amount of first and second blue laser light beams according to the exposure amount designation value. As a result, since the amount of illumination light is adjusted to a value that is appropriate for the imaging of the observation target, the amount of exposure when the sensor 48 images the observation target becomes the amount of exposure designated according to the exposure amount designation value. However, the amount of exposure can also be changed by adjusting the length of the charge accumulation period of the sensor 48 (so-called speed of an electronic shutter). For this reason, the exposure amount designation value calculation unit 65 may calculate the exposure amount designation value that designates the length of the charge accumulation period instead of the exposure amount designation value that designates the amount of illumination light. In this case, the exposure amount designation value is input to the imaging control unit 49, and the imaging control unit 49 adjusts the charge accumulation period of the sensor 48 according to the input exposure amount designation value. The exposure amount designation value calculation unit 65 may calculate the exposure amount designation value that designates the amount of illumination light and the length of the charge accumulation period, and may change the amount of exposure by designating the amount of illumination light and the length of the charge accumulation period.

When the observation mode selector SW 22b is set to the normal observation mode, the image processing switching unit 60 inputs the image signals to the normal observation image processing unit 62. On the other hand, when the observation mode selector SW 22b is set to the special observation mode, the image processing switching unit 60 inputs the image signals to the special observation image processing unit 64.

The normal observation image processing unit 62 includes a color conversion section 68, a color enhancement section 70, a structure enhancement section 72, and a display image signal generation section 73. The color conversion section 68 generates RGB image data by assigning the input RGB image signals of one frame to R, G, and B pixels. Then, color conversion processing, such as 3×3 matrix processing, gradation conversion processing, and three-dimensional LUT processing, is performed on the RGB image data.

The color enhancement section 70 performs various kinds of color enhancement processing on the RGB image data after the color conversion processing. The structure enhancement section 72 performs structure enhancement processing, such as spatial frequency enhancement, on the RGB image data after the color enhancement processing. The RGB image data subjected to the structure enhancement processing by the structure enhancement section 72 is input to the display image signal generation section 73 as a normal observation image. The display image signal generation section 73 converts the normal observation image into a display format signal (display image signal; for example, the brightness signal Y and the color difference signals Cb and Cr), and inputs the display format signal to the monitor 18. As a result, the normal observation image is displayed on the monitor 18.

As shown in FIG. 8, the special observation image processing unit 64 includes a signal ratio calculation section 81, a correlation storage section 82, an oxygen saturation calculation section 83, a region detection section 84, a threshold value calculation section 85, and an oxygen saturation image generation section 86.

The signal ratio calculation section 81 calculates a signal ratio that is used when the oxygen saturation calculation section 83 calculates the oxygen saturation. Specifically, the signal ratio calculation section 81 calculates the signal ratio B1/G2 between the B1 image signal and the G2 image signal for each pixel, and calculates the signal ratio R2/G2 between the R2 image signal and the G2 image signal for each pixel. When calculating the signal ratio B1/G2, the signal ratio calculation section 81 uses the B1 image signal that is corrected to the signal value mostly based on only the first blue laser light by performing correction processing for enhancing the color separability by removing the signal value based on the first fluorescence from the B1 image signal by inter-pixel calculation using the B1 image signal, the G1 image signal, and the R1 image signal.

Figure 9:
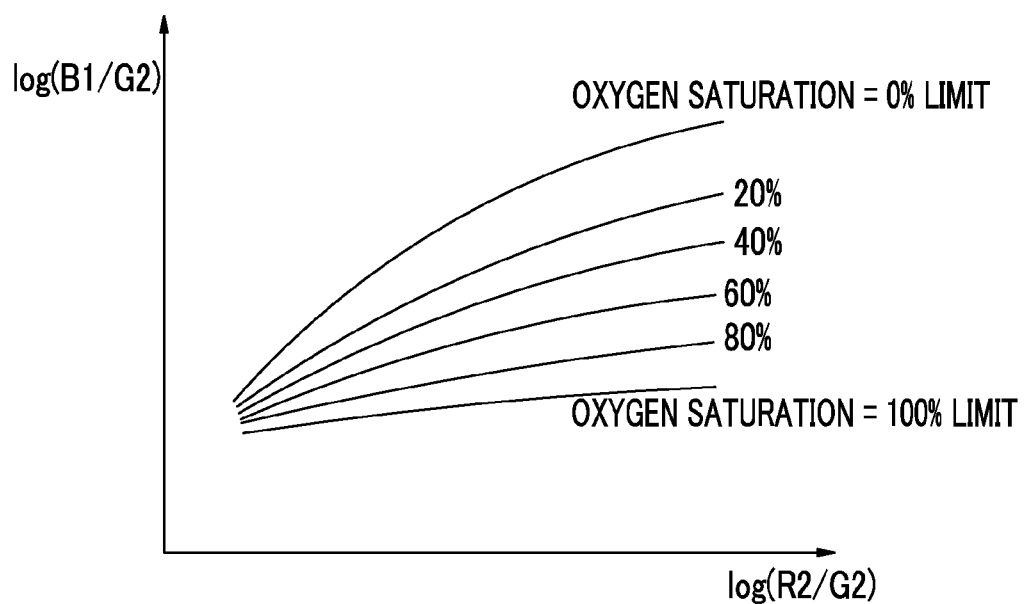
FIG. 9 is a graph showing the correlation between the signal ratio and the oxygen saturation.

The correlation storage section 82 stores a correlation between the signal ratio calculated by the signal ratio calculation section 81 and the oxygen saturation. This correlation is stored in a two-dimensional table that defines the isolines of the oxygen saturation on a two-dimensional space shown in FIG. 9. The position and shape of the isolines for the signal ratio are obtained in advance by physical simulation of light scattering, and the distance between isolines changes according to the blood volume (horizontal axis in FIG. 9). The correlation between the signal ratio and the oxygen saturation is stored in a log scale.

Figure 10:
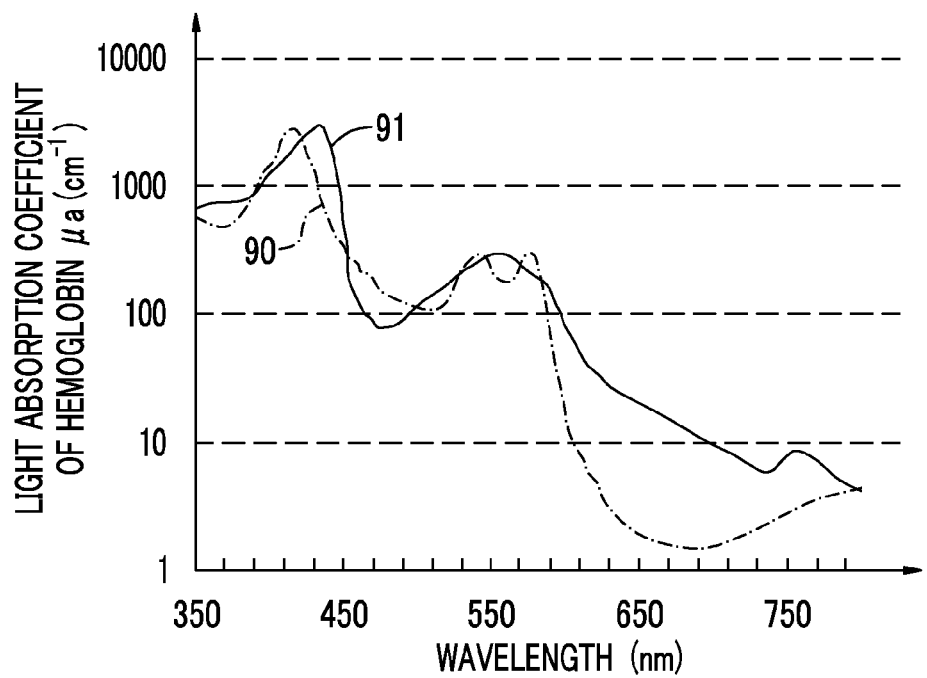
FIG. 10 is a graph showing the absorption coefficients of oxygenated hemoglobin and reduced hemoglobin.

As shown in FIG. 10, this correlation is closely related to the absorption characteristics or light scattering characteristics of oxygenated hemoglobin (graph 90) or reduced hemoglobin (graph 91). For example, as in a wavelength range near 473 nm that is the center wavelength of the first blue laser light, in a wavelength range where the difference between the absorption coefficient of oxygenated hemoglobin and the absorption coefficient of reduced hemoglobin is large, that is, in a wavelength range where the absorption coefficient changes according to the oxygen saturation of blood hemoglobin, it is easy to handle the information of the oxygen saturation. However, the B1 image signal including a signal corresponding to 473-nm light has a high dependence not only on the oxygen saturation but also on the blood volume. Therefore, by using the signal ratio R2/G2 obtained from the R2 image signal and the G2 image signal as well as the B1 image signal, it is possible to accurately calculate the oxygen saturation without there being dependency on the blood volume. Here, the G2 image signal corresponds to light that changes mainly depending on the blood volume, and the R2 image signal is a reference signal of the B1 image signal and the G2 image signal.

Figure 11:
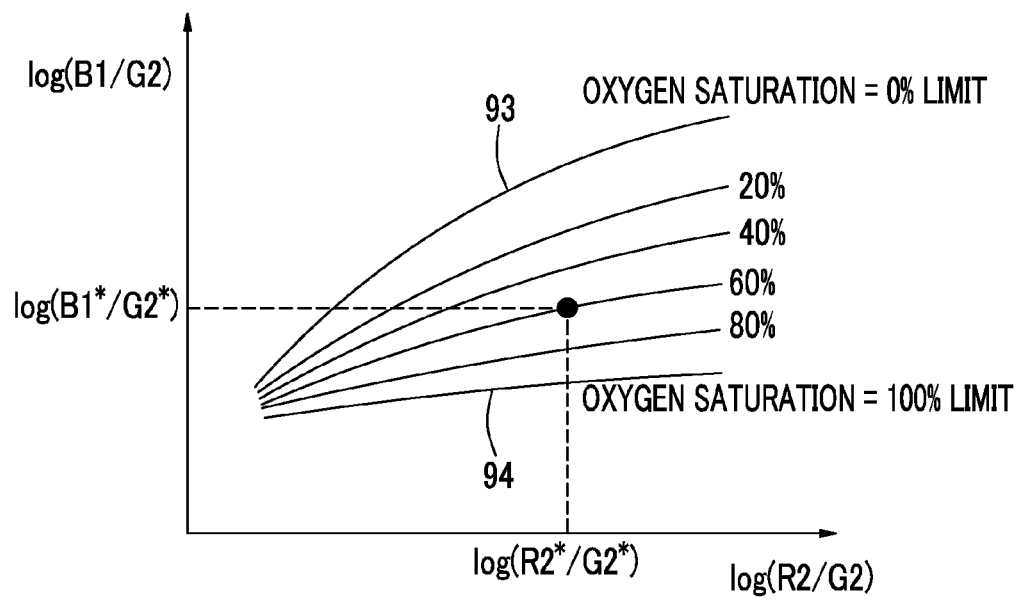
FIG. 11 is an explanatory diagram showing a method of calculating the oxygen saturation.

The oxygen saturation calculation section 83 calculates the oxygen saturation based on the image signals by using the signal ratio calculated by the signal ratio calculation section 81. More specifically, the oxygen saturation calculation section 83 calculates the oxygen saturation corresponding to the signal ratio calculated by the signal ratio calculation section 81, for each pixel, with reference to the correlation stored in the correlation storage section 82. For example, when the signal ratio B1/G2 and the signal ratio R2/G2 in a specific pixel are B1*/G2* and R2*/G2*, respectively, the oxygen saturation corresponding to the signal ratio B1*/G2* and the signal ratio R2*/G2* is "60%" when the correlation shown in FIG. 11 is referred to. Accordingly, the oxygen saturation calculation section 83 calculates the oxygen saturation of the specified pixel as "60%".

In addition, a case where the signal ratio B1/G2 and the signal ratio R2/G2 become extremely large or extremely small hardly occurs. That is, a case hardly occurs in which the value of the signal ratio B1/G2 or the signal ratio R2/G2 exceeds the lower limit line 93 of the oxygen saturation of 0% or on the contrary becomes lower than the upper limit line 94 of the oxygen saturation of 100%. Here, the oxygen saturation calculation section 83 sets the oxygen saturation to 0% when the calculated oxygen saturation is lower than the lower limit line 93, and sets the oxygen saturation to 100% when the calculated oxygen saturation exceeds the upper limit line 94. When a point corresponding to the signal ratio B1/G2 and the signal ratio R2/G2 deviates from a region between the lower limit line 93 and the upper limit line 94, display showing that the reliability of the oxygen saturation in the pixel is low may be performed, or the oxygen saturation may not be calculated.

The region detection section 84 detects a first region within the range where the pixel value is determined by the threshold value and a second region out of the range where the pixel value is determined by the threshold value by acquiring the image signal from the image processing switching unit 60 and comparing the pixel value of the acquired image signal with a threshold value. In the present embodiment, the threshold value used in the region detection section 84 is a value $Q_{TH}$ as a reference for dividing to which of the first and second regions each pixel belongs. In addition, the first region is a region including one or more pixels having pixel values equal to or less than the threshold value $Q_{TH}$, and the second region is a region including one or more pixels having pixel values equal to or greater than the threshold value $Q_{TH}$. For this reason, the first and second regions may be detected at a plurality of positions. Alternatively, only the first region or only the second region may be detected. Information regarding the position or range of the first and second regions detected by the region detection section 84 is input to the oxygen saturation image generation section 86, and is used to generate an oxygen saturation image.

Figure 12:
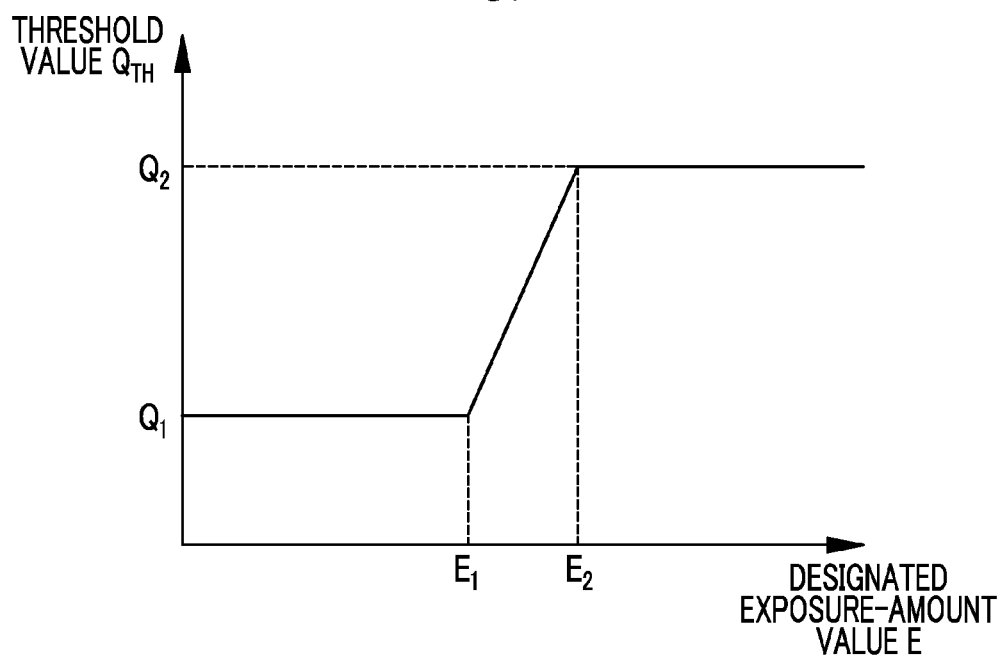
FIG. 12 is a graph showing the relationship between the exposure amount designation value and the threshold value.

The threshold value calculation section 85 calculates a threshold value, which is used for detection of the first and second regions in the region detection section 84, according to the exposure amount designation value acquired from the exposure amount designation value calculation unit 65. The threshold value calculation section 85 increases the threshold value as the exposure amount designation value increases. In the present embodiment, as shown in FIG. 12, the threshold value $Q_{TH}$ calculated by the threshold value calculation section 85 is one of a first threshold value $Q_1$, a second threshold value $Q_2$ that is larger than the first threshold value $Q_1$, and a value (hereinafter, referred to as an intermediate value) that changes linearly according to an exposure amount designation value E between the first threshold value $Q_1$ and the second threshold value $Q_2$. The method of changes in the first threshold value $Q_1$, the second threshold value $Q_2$, and the threshold value between the first and second threshold values $Q_1$ and $Q_2$ is determined in advance by an experiment or the like.

More specifically, the threshold value calculation section 85 sets the first threshold value $Q_1$ as the threshold value $Q_{TH}$ used in the region detection section 84 when the exposure amount designation value E is equal to or less than a first specific value $E_1$ set in advance. In addition, the threshold value calculation section 85 performs comparison with a second specific value $E_2$ set in advance to a value larger than the first specific value $E_1$. When the exposure amount designation value E is larger than the second specific value $E_2$, the threshold value calculation section 85 sets the second threshold value $Q_2$ as the threshold value $Q_{TH}$ used in the region detection section 84. When the exposure amount designation value E is larger than the first specific value $E_1$ and is smaller than the second specific value $E_2$, the threshold value calculation section 85 calculates a value that changes linearly with respect to the exposure amount designation value E between the first threshold value $Q_1$ and the second threshold value $Q_2$, and sets the value as the threshold value $Q_{TH}$ used in the region detection section 84. For example, when the exposure amount designation value E is an average value $((E_1+E_2)/2)$ of the first and second specific values $E_1$ and $E_2$, the threshold value calculation section 85 sets an average value $((Q_1+Q_2)/2)$ of the first and second threshold values $Q_1$ and $Q_2$ as the threshold value $Q_{TH}$ used in the region detection section 84.

The threshold value $Q_{TH}$ calculated according to the exposure amount designation value E as described above is closely related to the observation distance and the risk of artifacts. First, when a case of performing remote imaging in a state where the distal portion 24 and an observation target 96 are spaced apart from each other as shown in FIG. 13A is compared with a case of performing imaging in a state where the distal portion 24 and the observation target 96 are close to each other as shown in FIG. 13B, assuming that a fixed amount of illumination light is emitted, the amount of exposure is small at the time of remote imaging and large at the time of near-distance imaging. Accordingly, for example, the brightness of the normal observation image is almost constant regardless of the observation distance by adjusting the amount of exposure automatically based on the exposure amount designation value E. However, the exposure amount designation value E used for the adjustment of the amount of exposure is increased at the time of remote imaging but is reduced at the time of near-distance imaging.

Second, when there is no dirt or the like on the mucous membrane and a fixed amount of illumination light is emitted to the observation target, error occurs in the oxygen saturation at the time of near-distance imaging. In this case, when an oxygen saturation image showing the oxygen saturation is generated, artifacts may appear in the oxygen saturation image. However, when the observation distance is large, artifacts hardly appear because the error of the oxygen saturation is small. In particular, as shown in FIG. 14, the risk that artifacts will appear in the oxygen saturation image is high at the time of near-distance imaging at a specific observation distance or less and low at the time of remote imaging.

Therefore, it can be said that the observation distance is large and accordingly artifacts hardly appear when the exposure amount designation value E is large and that the observation distance is small and accordingly artifacts are likely to appear when the exposure amount designation value E is small. Based on this relationship, the threshold value calculation section 85 makes the first threshold value $Q_1$, which is a smaller one of the two threshold values $Q_1$ and $Q_2$, be used in the region detection section 84 when the risk that artifacts will appear in the oxygen saturation image is high and the second threshold value $Q_2$, which is a larger one, be used in the region detection section 84 when the risk that artifacts will appear in the oxygen saturation image is low. When the risk that artifacts will appear in the oxygen saturation image is between the above risks, the threshold value calculation section 85 makes the intermediate value be used in the region detection section 84.

To be more precise, the observation distance is different between the respective pixels of the image signal. For example, in FIGS. 13A and 13B, when the observation distance in the middle of the imaging range (indicated by the dashed line) of the observation target 96 is compared with the observation distance at the end of the imaging range, the observation distance in the middle of the imaging range is relatively short, and the observation distance at the end of the imaging range is longer than the observation distance in the middle of the imaging range. For this reason, the threshold value $Q_{TH}$ can be regarded as indicating the pixel value of the pixel at the average (or representative) observation distance when imaging the observation target 96 and the average likelihood of the appearance of artifacts when the image signal is used for the calculation of the oxygen saturation. Accordingly, when the threshold value $Q_{TH}$ is compared with the pixel value of each pixel of the image signal, the threshold value $Q_{TH}$ becomes a reference that distinguishes a region having a short observation distance in the image signal and having a pixel in which artifacts are likely to appear from a region having a long observation distance in the same image signal and having a pixel in which artifacts are difficult to appear. The region detection of the region detection section 84 uses this. The first region is a region having a short observation distance in the image signal and having a pixel in which artifacts are likely to appear, and the second region is a region having a long observation distance in the same image signal and having a pixel in which artifacts are difficult to appear.

In the present embodiment, the threshold value calculation section 85 calculates the threshold value $Q_{TH}$ stepwise according to the graph in FIG. 12 as described above. However, the threshold value $Q_{TH}$ is preferably determined by the linear relationship with the exposure amount designation value E so that the threshold value $Q_{TH}$ is large when the exposure amount designation value E is large and the threshold value $Q_{TH}$ is small when the exposure amount designation value E is small in general.

The oxygen saturation image generation section 86 generates an oxygen saturation image showing the oxygen saturation in a pseudo color using the oxygen saturation calculated by the oxygen saturation calculation section 83 and the information of the first and second regions detected by the region detection section 84, and displays the oxygen saturation image on the monitor 18. Specifically, first, the oxygen saturation image generation section 86 acquires a B2 image signal, a G2 image signal, and an R2 image signal, and assigns these image signals to a B pixel, a G pixel, and an R pixel, respectively, to generate RGB image data. Then, color conversion processing, such as 3×3 matrix processing, gradation conversion processing, and three-dimensional LUT processing, is performed on the RGB image data, and structure enhancement processing, such as spatial frequency enhancement, is further performed depending on the setting or the like. Then, the RGB image data subjected to these various kinds of processing is converted into an image signal (hereinafter, referred to as a primary image signal) configured to include the brightness signal Y and the color difference signals Cb and Cr. That is, the oxygen saturation image generation section 86 first generates the same RGB image data as a normal observation image using the B2 image signal, the G2 image signal, and the R2 image signal, and acquires a primary image signal corresponding to the display image signal of the normal observation image.

Then, the oxygen saturation image generation section 86 generates a secondary image signal showing the oxygen saturation in a pseudo color by replacing the signal values of the color difference signals Cb and Cr of the primary image signal with the oxygen saturation based on the information of the first and second regions, and displays the secondary image signal on the monitor 18. An image shown by the secondary image signal after replacing the color difference signals Cb and Cr is the oxygen saturation image.

Figure 15:
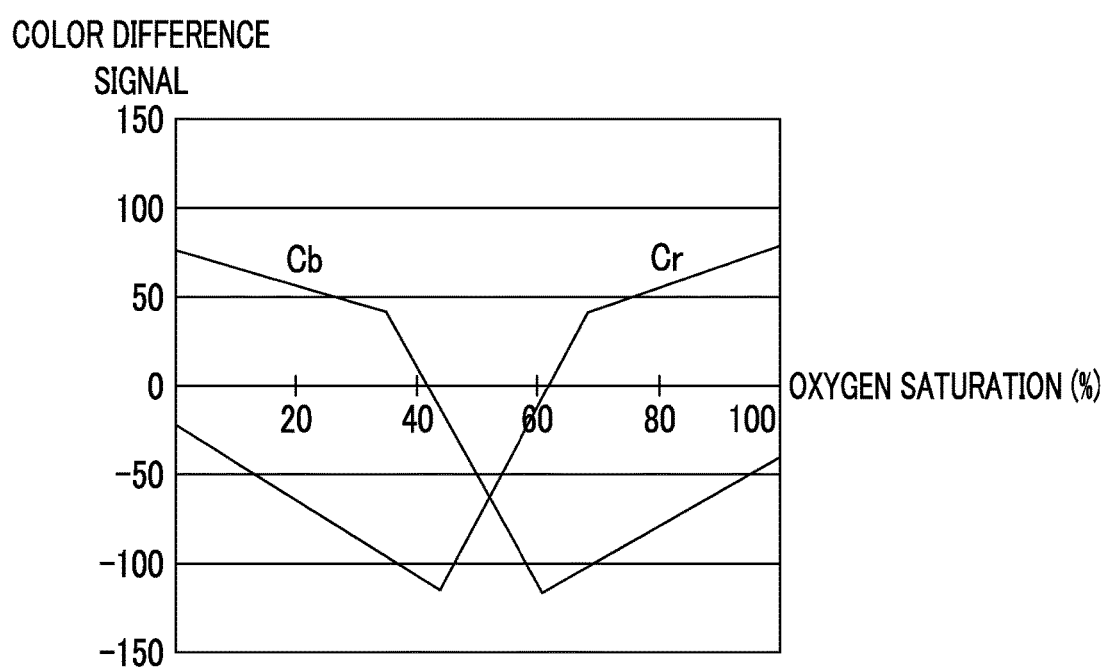
FIG. 15 is a graph showing the relationship between the oxygen saturation and the color difference signal.

More specifically, the oxygen saturation image generation section 86 has a color table 87 in which the oxygen saturation and color difference signals are associated with each other. The oxygen saturation image generation section 86 replaces the color difference signals Cb and Cr of each pixel in the second region of the primary image signal with the color difference signals Cb and Cr corresponding to the blood volume and the oxygen saturation according to the color table 87. As shown in FIG. 15, the color table 87 is defined such that the signal value of the color difference signal Cb is negative and the signal value of the color difference signal Cr is positive when the oxygen saturation is high and the signal value of the color difference signal Cb is positive and the signal value of the color difference signal Cr is negative when the oxygen saturation is low. In addition, the color table 87 is defined such that the magnitude relationship between the signal value of the color difference signal Cb and the signal value of the color difference signal Cr is reversed at the intermediate oxygen saturation. For this reason, if the color difference signals Cb and Cr of the color table 87 are used according to the oxygen saturation, the color of each pixel is changed to blue, light blue, green, yellow, orange, and red as the oxygen saturation increases.

On the other hand, the oxygen saturation image generation section 86 replaces the signal values of the color difference signals Cb and Cr of each pixel in the first region of the primary image signal with zero regardless of the value of the oxygen saturation of each pixel. Accordingly, in the oxygen saturation image, pixels of the first region are expressed in an achromatic color. Thus, since the pixels of the second region are expressed in a pseudo color according to the color table 87 while the pixels of the first region are expressed with an achromatic color, the oxygen saturation image indicates that the calculation accuracy of the oxygen saturation of the first region is low.

Figure 16:
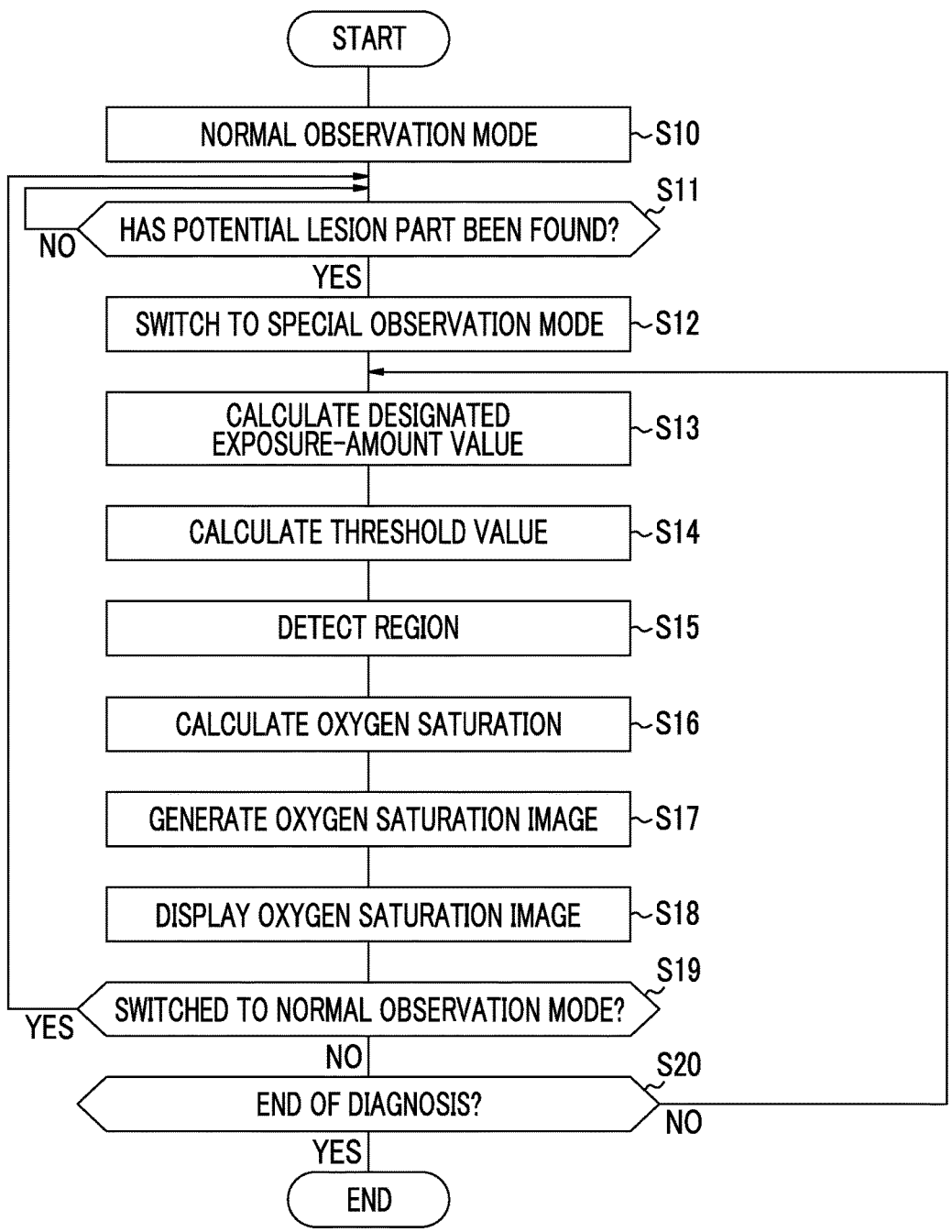
FIG. 16 is a flowchart showing the operation of the endoscope system.

Next, the flow of observation using the endoscope system 10 according to the present embodiment will be described with reference to the flowchart in FIG. 16. First, in the normal observation mode, screening is performed from the most distant view state (S10). In the normal observation mode, a normal observation image is displayed on the monitor 18. When a part that is likely to be a lesion (hereinafter, referred to as a potential lesion part), such as a brownish area or rubor, is found in this screening (S11), the mode selector SW 22b is operated for switching to the special observation mode (S12). Then, in the special observation mode, the potential lesion part is diagnosed.

In the special observation mode, the first and second white light beams are alternately emitted to the observation target in synchronization with the imaging frame of the sensor 48 (illumination light generation step). Accordingly, the sensor 48 outputs the R1 image signal, the G1 image signal, and the B1 image signal in the first frame, and outputs the R2 image signal, the G2 image signal, and the B2 image signal in the second frame. These image signals are acquired by the image signal acquisition unit 54 of the processor device 16 (image signal acquisition step), and various kinds of signal processing are performed by the image signal acquisition unit 54.

Then, the exposure amount designation value calculation unit 65 calculates the exposure amount designation value E based on the image signals output from the image signal acquisition unit 54 (S13: exposure amount designation value calculation step). The light source control unit 40 adjusts the amount of illumination light emitted to the observation target 96 automatically based on the exposure amount designation value E.

Then, the threshold value calculation section 85 calculates the threshold value $Q_{TH}$ according to the exposure amount designation value E (S14: threshold value calculation step). After the threshold value $Q_{TH}$ is calculated, the region detection section 84 compares the pixel value of each pixel of the image signal with the threshold value $Q_{TH}$, and detects a first region having a pixel value equal to or less than the threshold value $Q_{TH}$ and a second region having a pixel value equal to or greater than the threshold value $Q_{TH}$ (S15: region detection step).

Figure 17:
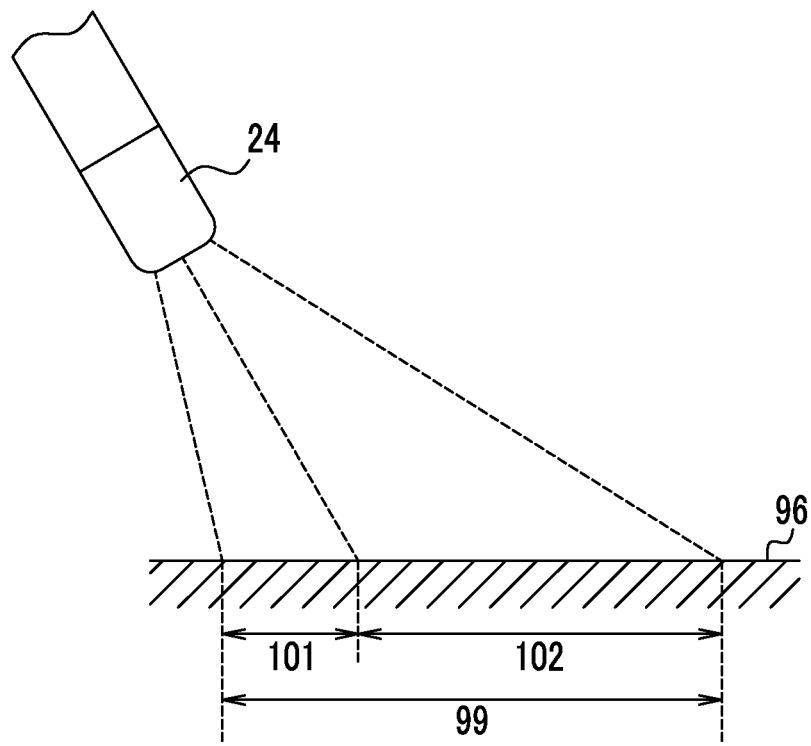
FIG. 17 is an explanatory diagram showing first and second regions when the observation distance is long.

As described above, the endoscope system 10 calculates the threshold value $Q_{TH}$ according to the exposure amount designation value E and detects the first and second regions based on the threshold value $Q_{TH}$ according to the exposure amount designation value E. Since the threshold value $Q_{TH}$ is calculated according to the exposure amount designation value E, the threshold value $Q_{TH}$ is a value relevant to the observation distance and the risk of artifacts appearing in the oxygen saturation image. Therefore, when the pixel value is compared with the threshold value $Q_{TH}$ to detect the first and second regions, for example, as shown in FIG. 17, a region where artifacts are likely to appear in an observation range 99 is detected as a first region 101, and a region where artifacts are difficult to appear is detected as a second region 102. At the observation distance shown in FIG. 17, the distal portion 24 is far from the observation target 96. Therefore, assuming that the exposure amount designation value E is equal to or greater than the second specific value $E_2$, the second threshold value $Q_2$ is used as the threshold value $Q_{TH}$.

Figure 18:
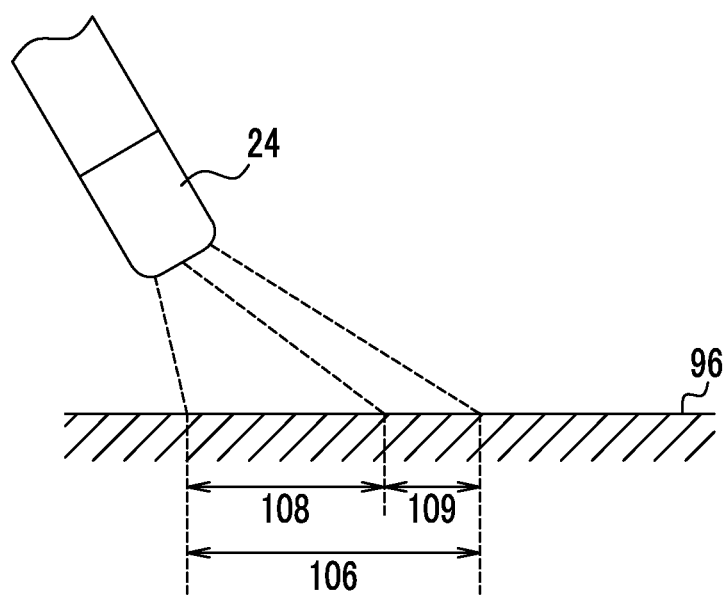
FIG. 18 is an explanatory diagram showing first and second regions when the observation distance is short.

Similarly, as shown in FIG. 18, also when the distal portion 24 is brought close to the observation target 96 compared with FIG. 17, a region where artifacts are likely to appear in an observation range 106 at the observation distance is detected as a first region 108, and a region where artifacts are difficult to appear is detected as a second region 109. In addition, when the distal portion 24 is brought close to the observation target 96, the exposure amount designation value E is reduced. Therefore, at the observation distance shown in FIG. 18, assuming that the exposure amount designation value E is equal to or less than the first specific value $E_1$, the first threshold value $Q_1$ is used as the threshold value $Q_{TH}$.

Figure 19:
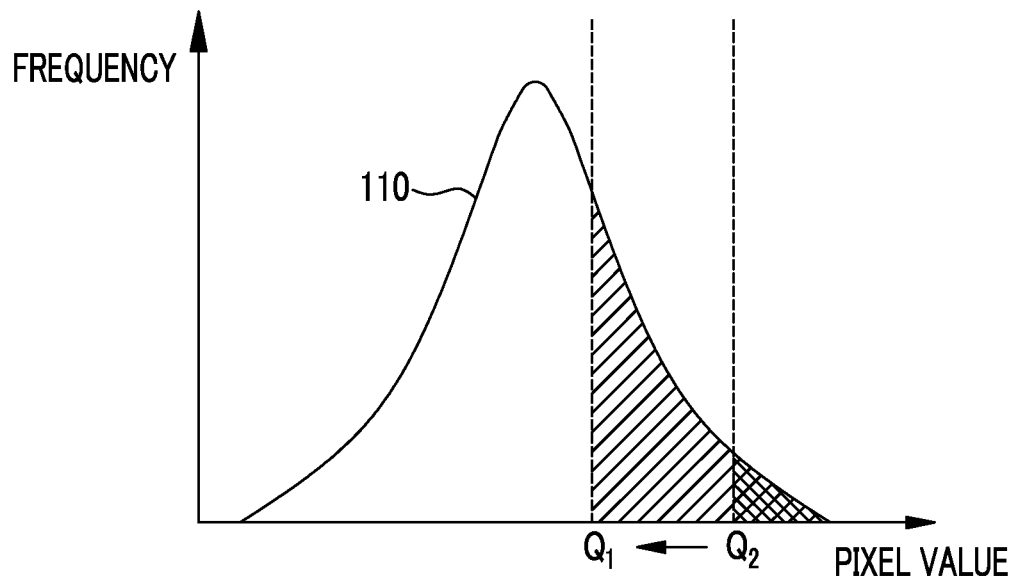
FIG. 19 is an explanatory diagram showing the frequency histogram of a pixel value and the relationship with a threshold value.

As shown in FIG. 19, when the distal portion 24 is brought close to the observation target and accordingly the exposure amount designation value E is reduced, the threshold value $Q_{TH}$ is changed from the threshold value $Q_2$ to the threshold value $Q_1$ for a frequency histogram 110 of pixel values. As a result, as indicated by oblique lines, the number of pixels detected as a first region is increased, and the number of pixels detected as a remaining second region is decreased. On the contrary, if the distal portion 24 is located away from the observation target 96, the number of pixels detected as a first region is decreased, and the number of pixels detected as a second region is increased.

Therefore, when FIG. 17 in which the observation distance is short is compared with FIG. 18 in which the observation distance is long, the ratio of the first region 108 to the observation range 106 in FIG. 18 is larger than the ratio of the first region 101 to the observation range 99 in FIG. 17. That is, since the first and second regions are detected based on the threshold value $Q_{TH}$ calculated according to the exposure amount designation value E, the first region widens and the second region narrows as the observation distance decreases. Thus, the endoscope system 10 detects appropriately the first region where artifacts are likely to appear and the second region where artifacts are difficult to appear.

The first and second regions are detected as described above, and the signal ratio calculation section 81 calculates the signal ratios B1/G2 and R2/G2 based on the image signals output from the image signal acquisition unit 54. Based on these signal ratios, the oxygen saturation calculation section 83 calculates the oxygen saturation for each pixel (S16: oxygen saturation calculation step).

When the first and second regions are detected and the oxygen saturation is calculated in this manner, the oxygen saturation image generation section 86 generates an oxygen saturation image based on the information of the first and second regions, the oxygen saturation, and the image signals output from the image signal acquisition unit 54 (S17: oxygen saturation image generation step), and the oxygen saturation image is displayed on the monitor 18 (S18).

Figure 20:
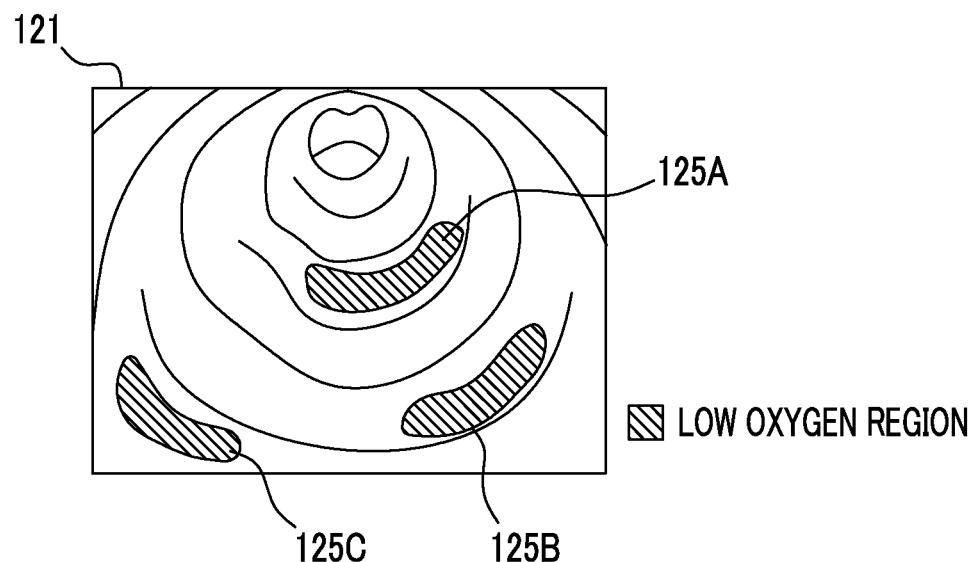
FIG. 20 is an oxygen saturation image when first and second regions are not added.

In a known endoscope system, oxygen saturation is pseudo-colored by the color difference signals Cb and Cr corresponding to the oxygen saturation according to the color table 87 without adding the information of the first and second regions. Accordingly, for example, as shown in FIG. 20, in an oxygen saturation image 121 generated by the known endoscope system, even if low oxygen regions 125A, 125B, and 125C where the oxygen saturation is pseudo-colored with blue due to low oxygen saturation are observed, the low oxygen regions 125A, 125B, and 125C may be false low oxygen regions appearing due to artifacts depending on the observation distance.

Figure 21:
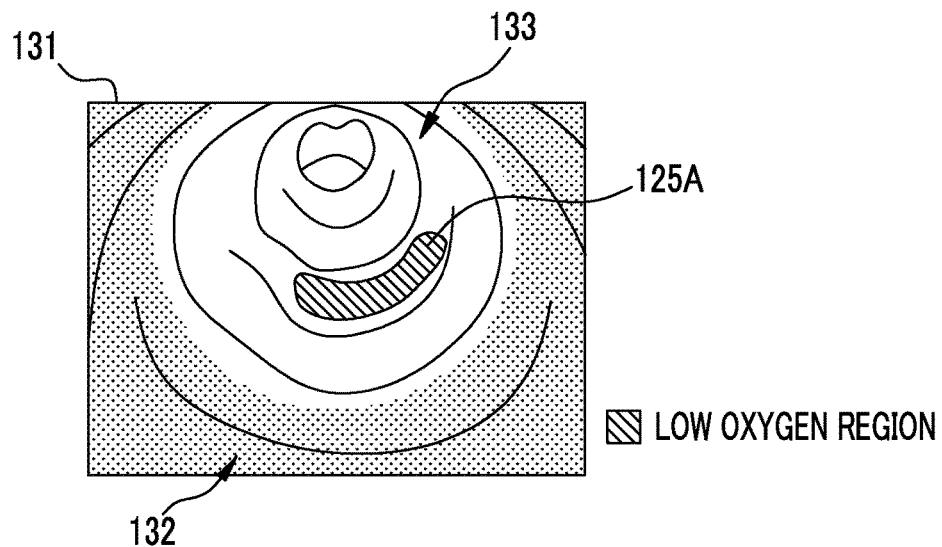
FIG. 21 is an oxygen saturation image when a display method is changed in the first and second regions.

On the other hand, as shown in FIG. 21, the endoscope system 10 detects a first region 132 and a second region 133. In the second region 133 at an observation distance where artifacts are difficult to appear, the endoscope system 10 performs pseudo-coloring with the color difference signals Cb and Cr corresponding to the oxygen saturation according to the color table 87 in the same manner as in the known endoscope system. However, in the first region 132 at an observation distance where artifacts are likely to appear, all of the color difference signals Cb and Cr are replaced with zero regardless of the oxygen saturation, and are displayed in an achromatic color. Accordingly, in the oxygen saturation image 131 generated and displayed by the endoscope system 10, a true low oxygen region 125A based on the properties of the observation target in the second region 133 is displayed. As indicated by hatching, the low oxygen regions 125B and 125C appearing due to artifacts of the first region 132 are achromatic and are not displayed.

Each of the above operations of the endoscope system 10 is switched to the normal observation mode (S19) or is repeatedly performed until the end of diagnosis (S20).

As described above, the endoscope system 10 can calculate the oxygen saturation, and acquire the information regarding a region where artifacts appear in the oxygen saturation image. In particular, since the threshold value $Q_{TH}$ for detecting the first and second regions is calculated according to the exposure amount designation value E, it is possible to detect the first and second regions appropriately according to the observation distance and the risk of artifacts that appear and to change the display method.

In the first embodiment, the color difference signals Cb and Cr of the first region where artifacts appear are replaced with zero. However, the values of the color difference signals Cb and Cr of the first region in the oxygen saturation image can be arbitrarily selected as long as the color of the pixel of the first region can be distinguished from the color of the pixel of the second region. That is, if the color difference signals Cb and Cr of the first region in the oxygen saturation image are replaced with signal values other than the combination of the color difference signals Cb and Cr used in the color table 87, both of the color difference signals Cb and Cr of the pixel of the first region do not necessarily need to be replaced with zero.

In the first embodiment, the first and second regions are detected by comparing the pixel value with the threshold value $Q_{TH}$ for each pixel. However, the first and second regions may also be detected by dividing an image signal into a plurality of blocks using a method set in advance and determining whether to set each of the blocks as a first region or a second region. For example, when dividing the image signal into nine blocks of 3×3, the region detection section 84 calculates an average value of pixel values (hereinafter, referred to as an average block pixel value) in the respective blocks. Then, the average block pixel value is compared with the threshold value $Q_{TH}$, and a block having an average block pixel value equal to or greater than the threshold value $Q_{TH}$ is detected as a first region and a block having an average block pixel value less than the threshold value $Q_{TH}$ is detected as a second region. Although the average block pixel value is compared with the threshold value $Q_{TH}$ in this modification, it is also possible to set the total value of the pixel values of the respective blocks as a calculation value based on the pixel value of each block and detect the first and second regions based on the calculation value. In this case, it is preferable to change the magnitude of the threshold value $Q_{TH}$ to a value according to the calculation value to be compared.

In the first embodiment, the first and second regions are detected based on the magnitude of the pixel value. However, the first and second regions may also be detected based on a value obtained by calculation based on the pixel value (hereinafter, referred to as a calculation value). For example, the region detection section 84 calculates an average value of the pixel values of all pixels (hereinafter, referred to as an all pixels average value), and calculates the ratio of the pixel value of each pixel to the all pixels average value (pixel value of each pixel/all pixels average value). It is also possible to detect the first and second regions by comparing the ratio with a threshold value $P_{TH}$. Similar to the threshold value $Q_{TH}$ for the pixel value in the first embodiment, it is preferable that the threshold value $P_{TH}$ to be compared with the ratio is set in advance according to the exposure amount designation value E. In addition, although the ratio of the pixel value to the all pixels average value is calculated as a calculation value in this modification, statistics, such as a deviation or a variation, may be used as the calculation value.

Second Embodiment

Figure 22:
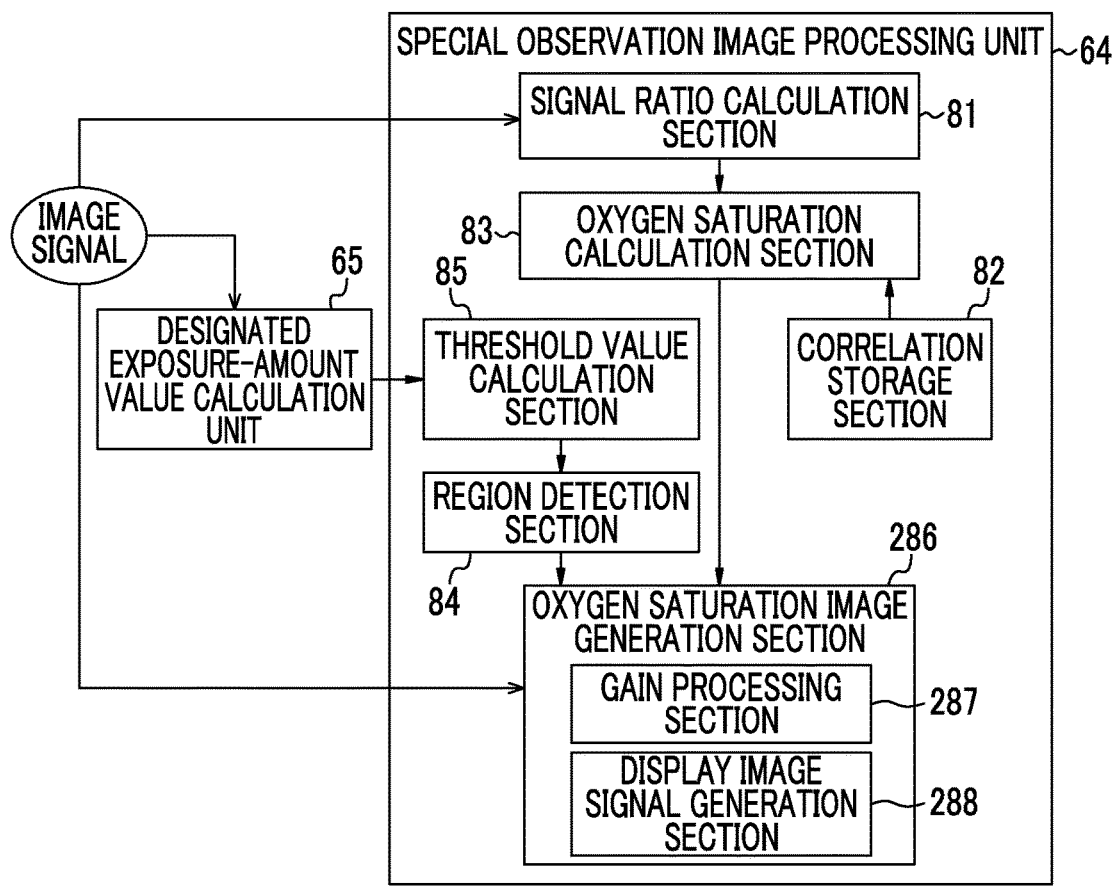
FIG. 22 is a block diagram of a special observation image processing unit of a second embodiment.

An endoscope system according to a second embodiment is formed by replacing the oxygen saturation image generation section 86 of the first embodiment with an oxygen saturation image generation section 286 shown in FIG. 22. Other configurations are the same as the endoscope system 10 according to the first embodiment.

The oxygen saturation image generation section 286 includes a gain processing section 287 and a display image signal generation section 288. The gain processing section 287 acquires a B2 image signal, a G2 image signal, and an R2 image signal, and multiplies these image signals by the gain corresponding to the oxygen saturation for each pixel. For example, in a pixel where the corrected oxygen saturation is 60% or more, the gain processing section 287 multiplies all of the B2 image signal, the G2 image signal, and the R2 image signal by the same gain "1". In contrast, in a pixel where the corrected oxygen saturation is less than 60%, the gain processing section 287 multiplies the B2 image signal by the gain less than "1" and multiplies the G2 image signal and the R2 image signal by the gain of "1" or more.

The display image signal generation section 288 generates RGB image data by using the B2 image signal, the G2 image signal, and the R2 image signal after gain multiplication by the gain processing section 287. Then, the generated RGB image data is converted into the brightness signal Y and the color difference signals Cb and Cr by performing YC conversion processing. Then, a display image signal is generated by replacing the signal values of the color difference signals Cb and Cr of the pixel belonging to the first region with zero. An image shown by the display image signal is the oxygen saturation image.

Figure 23:
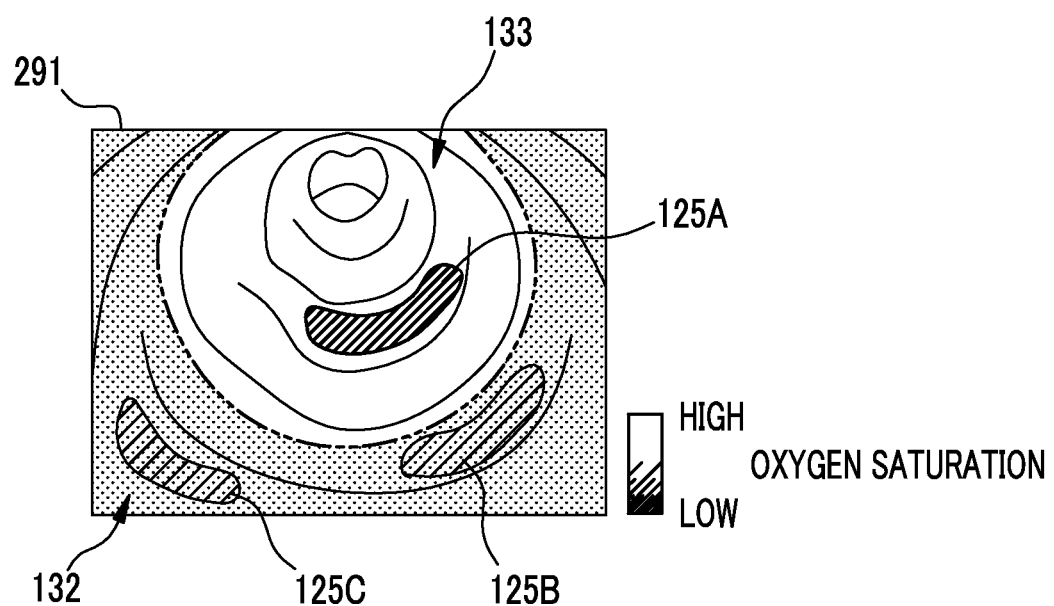
FIG. 23 is an oxygen saturation image in a second embodiment.

FIG. 23 shows an oxygen saturation image 291 that is shown by the display image signal generated by the oxygen saturation image generation section 286. In the oxygen saturation image 291, in the second region 133 where no artifact appears, a high oxygen region where the oxygen saturation exceeds a specific value (region having an oxygen saturation of 60% to 100%) is expressed in the same color as a normal observation image, and a low oxygen region where the oxygen saturation is less than the specific value (region having an oxygen saturation of 0% to 60%) is expressed in a different color (pseudo color) from the normal observation image. That is, in the oxygen saturation image shown by the display image signal, only the low oxygen region is partially pseudo-colored.

On the other hand, regardless of a high oxygen region or a low oxygen region, a pixel belonging to the first region 132 where artifacts appear is expressed in an achromatic color. Accordingly, the oxygen saturation image 291 is the same as the oxygen saturation image 131 (refer to FIG. 21) of the first embodiment in that the true low oxygen region 125A based on the properties of the observation target in the second region 133 is displayed in a pseudo color. However, in the oxygen saturation image 291 of the second embodiment, the low oxygen regions 125B and 125C appearing due to artifacts of the first region 132 are also displayed, but the color is an achromatic color. Therefore, it is possible to display that the low oxygen regions 125B and 125C are low oxygen regions appearing due to artifacts. Therefore, by observing the oxygen saturation image 291, it is possible to calculate the oxygen saturation and acquire the information regarding a region where artifacts appear.

In FIG. 23, the level of oxygen saturation is expressed with the density of hatched oblique lines, and the density of hatched oblique lines becomes high as the oxygen saturation becomes low.

In addition, although the image generation section 84 performs gain multiplication for pseudo coloring only for the low oxygen region in the second embodiment, a gain corresponding to the oxygen saturation may also be multiplied for the high oxygen region so that the entire oxygen saturation image is pseudo-colored. In addition, although the low oxygen region and the high oxygen region are divided at the oxygen saturation of 60%, this boundary can be arbitrarily selected.

Third Embodiment

Figure 24:
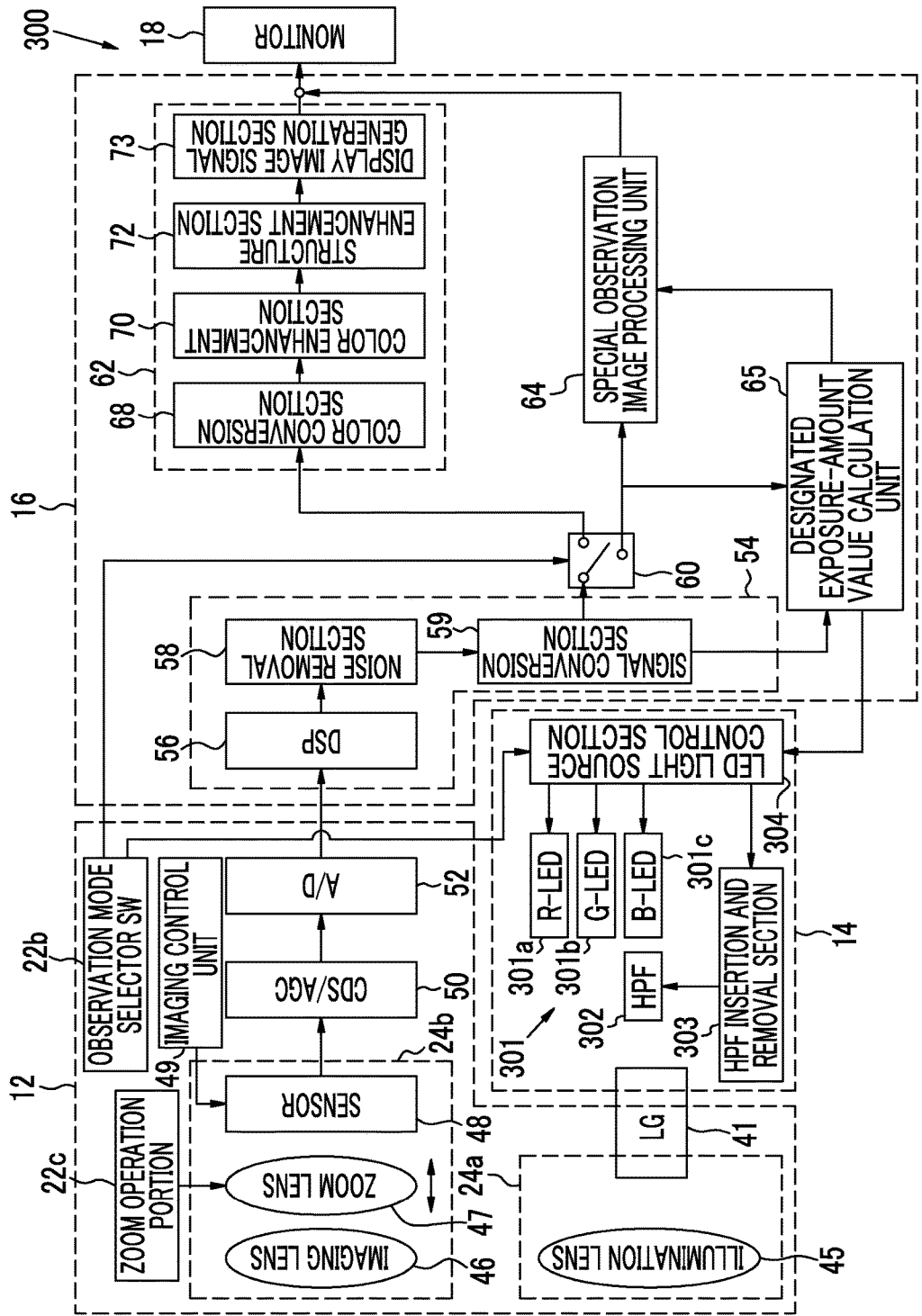
FIG. 24 is a block diagram of an endoscope system according to a third embodiment.

As shown in FIG. 24, in a light source device 14 of an endoscope system 300, a light emitting diode (LED) light source unit 301 and an LED light source control section 304 are provided instead of the first and second blue laser light sources 34 and 36 and the light source control unit 40. The phosphor 44 is not provided in an illumination optical system 24a of an endoscope system 300. Other than these, the endoscope system 300 is the same as the endoscope system 10 according to the first embodiment.

Figure 25:
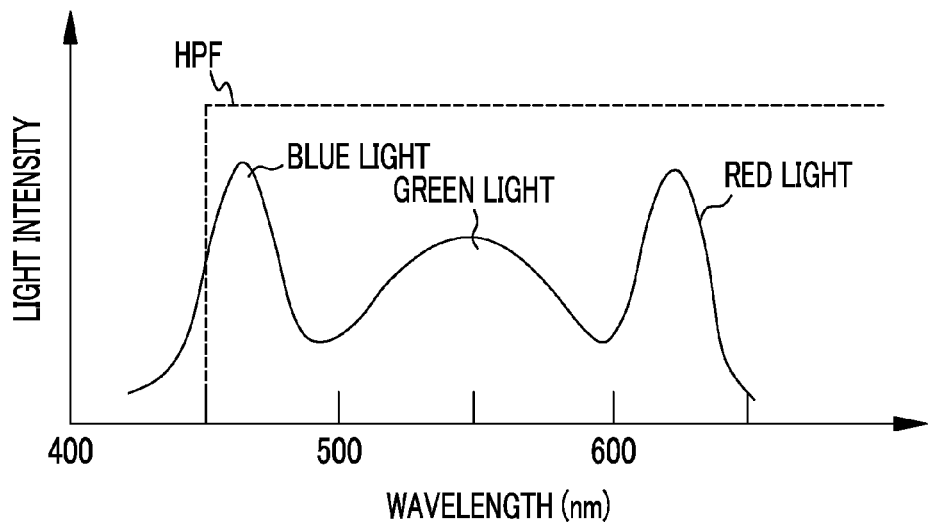
FIG. 25 is a graph showing the light emission band of an LED and the characteristics of an HPF.

The LED light source unit 301 includes an R-LED 301a, a G-LED 301b, and a B-LED 301c as light sources for emitting light limited to a specific wavelength band. As shown in FIG. 25, the R-LED 301a emits red band light (hereinafter, simply referred to as red light) having a wavelength of about 600 nm to 650 nm, for example. The center wavelength of the red light is about 620 nm to 630 nm. The G-LED 301b emits green band light (hereinafter, simply referred to as green light) having a wavelength of about 500 nm to 600 nm that is expressed by a normal distribution. The B-LED 301c emits blue band light (hereinafter, simply referred to as blue light) having a center wavelength of 445 nm to 460 nm.

The LED light source unit 301 includes a high pass filter (HPF) 302 that is removably inserted on the optical path of the blue light emitted from the B-LED 301c. The high pass filter 302 cuts the blue light having a wavelength in a wavelength band of about 450 nm or less, and allows light having a wavelength in a wavelength band higher than about 450 nm to be transmitted therethrough.

The cutoff wavelength (about 450 nm) of the high pass filter 302 is a wavelength at which the absorption coefficient of oxygenated hemoglobin and the absorption coefficient of reduced hemoglobin are almost equal (refer to FIG. 10), and the absorption coefficient of oxygenated hemoglobin and the absorption coefficient of reduced hemoglobin are reversed in the order of magnitude with the cutoff wavelength as a boundary. In the present embodiment, the correlation stored in the correlation storage section 82 is that the absorption coefficient of oxygenated hemoglobin is larger than the absorption coefficient of reduced hemoglobin. Accordingly, a signal based on the wavelength band equal to or lower than the cutoff wavelength is a cause by which incorrect oxygen saturation is calculated. Therefore, by preventing light having a wavelength in a wavelength band equal to or lower than the cutoff wavelength from being emitted to the observation target using the high pass filter 302 when acquiring at least the B1 image signal for calculating the oxygen saturation, the calculation accuracy of the oxygen saturation is improved.

Accordingly, the high pass filter 302 is inserted at the insertion position before the B-LED 301c in the special observation mode, and is retracted to the retraction position in the normal observation mode. The insertion and removal of the high pass filter 302 is performed by an HPF insertion and removal section 303 under the control of the LED light source control section 304.

Figure 26:
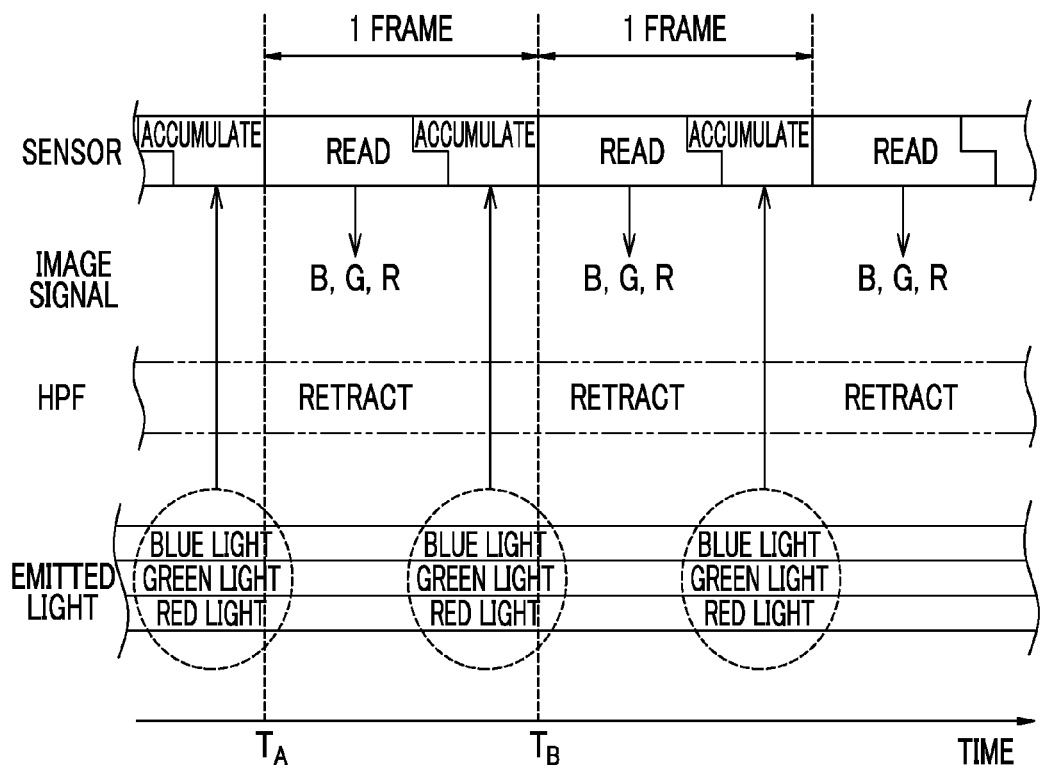
FIG. 26 is an explanatory diagram showing imaging control in the normal observation mode in the third embodiment.

The LED light source control section 304 controls ON/OFF and the amount of emitted light of the LEDs 301a to 301c of the LED light source unit 301 and the insertion and removal of the high pass filter 302. Specifically, as shown in FIG. 26, in the normal observation mode, the LED light source control section 304 turns on all of the LEDs 301a to 301c and retracts the high pass filter 302 from the optical path of the B-LED 301c. Accordingly, white light in which blue light, green light, and red light are superimposed are emitted to the observation target, and the sensor 48 images the observation target with reflected light of the white light and outputs an image signal of each color of B, and R.

Figure 27:
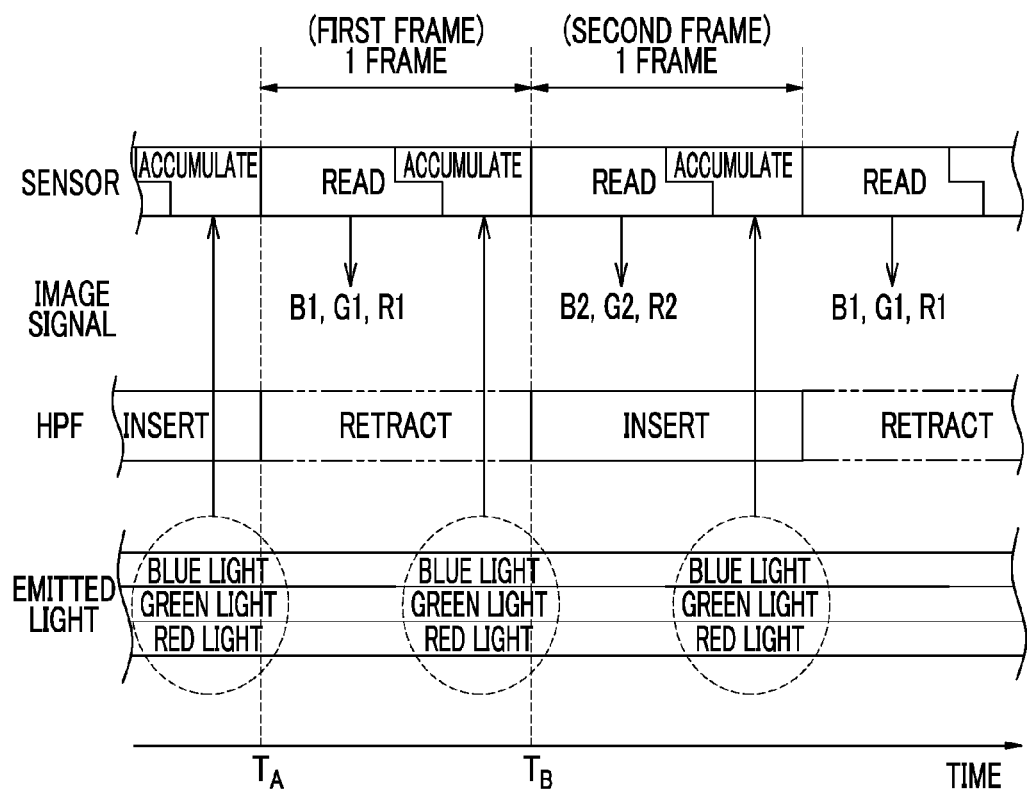
FIG. 27 is an explanatory view showing imaging control in the special observation mode in the third embodiment.

On the other hand, as shown in FIG. 27, in the special observation mode, the LED light source control section 304 inserts or retracts the high pass filter 302 for each frame in a state where all of the LEDs 301a to 301c are turned on. Accordingly, first mixed color light of blue light, green light, and red light when light having a wavelength in a wavelength band of 450 nm or less is cut off and second mixed color light of blue light, green light, and red light when light having a wavelength in a wavelength band of 450 nm or less is not cut off are alternately emitted to the observation target. The first mixed color light corresponds to the first white light in the first embodiment, and the second mixed color light corresponds to the second white light in the first embodiment.

Then, in the imaging control unit 49, a signal charge obtained by imaging the observation target under the first mixed color light is read in a reading period of the first frame, and the B1 image signal, the G1 image signal, and the R1 image signal are output. A signal charge obtained by imaging the observation target under the second mixed color light is read in a reading period of the second frame, and the B2 image signal, the G2 image signal, and the R2 image signal are output. Subsequent processing can be performed in the same manner as in the endoscope system 10.

The R-LED 301a, the G-LED 301b, the B-LED 301c, and the high pass filter 302 form an illumination unit that generates different illumination light beams that are emitted to the observation target.

Fourth Embodiment

Figure 28:
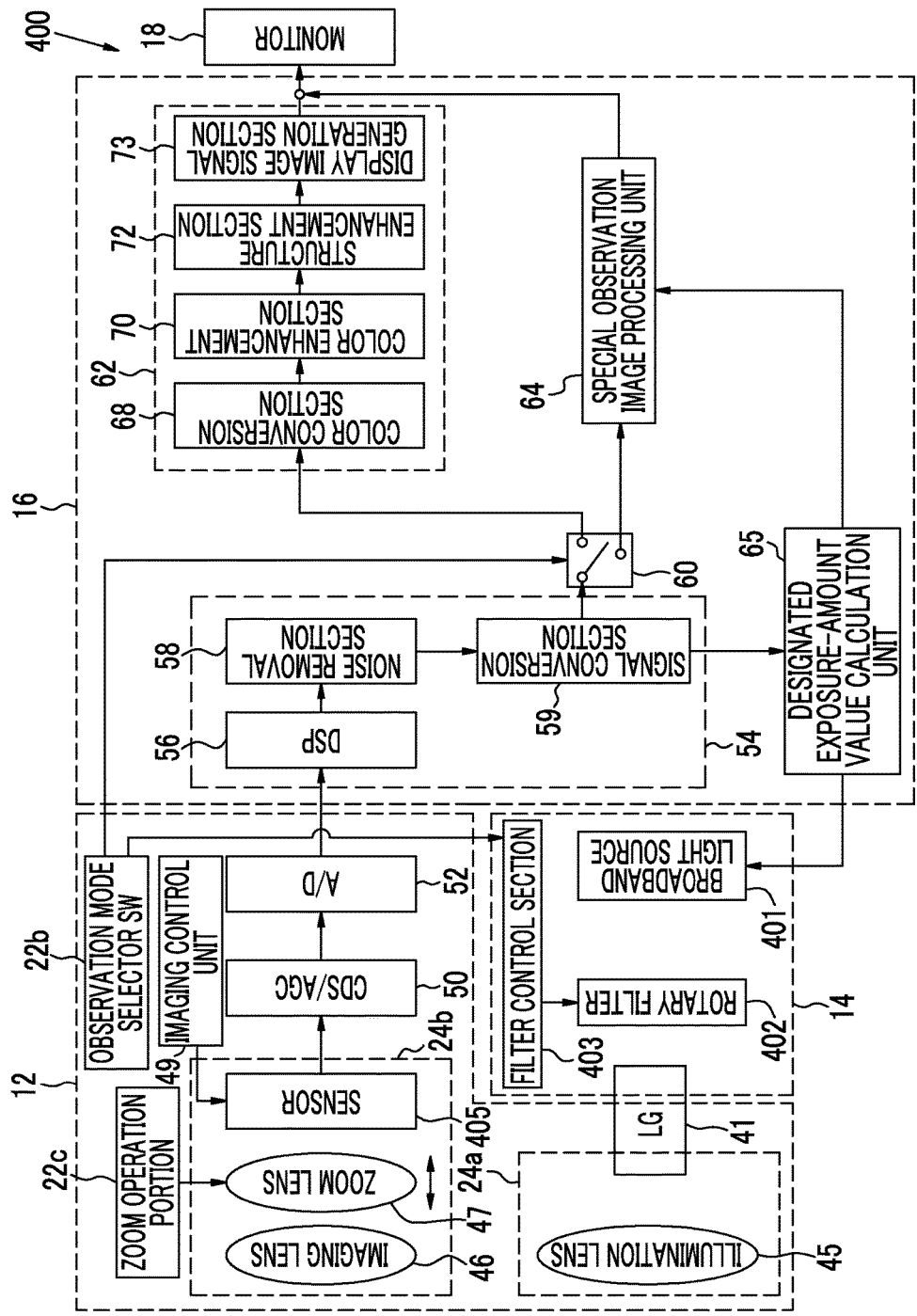
FIG. 28 is a block diagram of an endoscope system according to a fourth embodiment.

As shown in FIG. 28, in a light source device 14 of an endoscope system 400, a broadband light source 401, a rotary filter 402, and a rotary filter control section 403 are provided instead of the first and second blue laser light sources 34 and 36 and the light source control unit 40. A sensor 405 of the endoscope system 400 is a monochrome imaging device in which no color filter is provided. Therefore, the DSP 56 does not perform processing specific to the color imaging device, such as demosaic processing. Other than these, the endoscope system 400 is the same as the endoscope system 10 according to the first embodiment.

The broadband light source 401 is, for example, a xenon lamp or a white LED, and emits white light having a wavelength in a wavelength band ranging from blue to red. The rotary filter 402 includes a normal observation mode filter 410 and a special observation mode filter 411 (refer to FIG. 29), and can move in a radial direction between a first position for normal observation mode to place a normal observation mode filter 410 on the optical path, in which the white light emitted from the broadband light source 401 is incident on the light guide 41, and a second position for special observation mode to place a special observation mode filter 411 on the optical path. The movement of the rotary filter 402 to the first and second positions is controlled by the rotary filter control section 403 according to the selected observation mode. The rotary filter 402 rotates according to the imaging frame of the sensor 405 while being placed at the first or second position. The rotation speed of the rotary filter 402 is controlled by the rotary filter control section 403 according to the selected observation mode.

Figure 29:
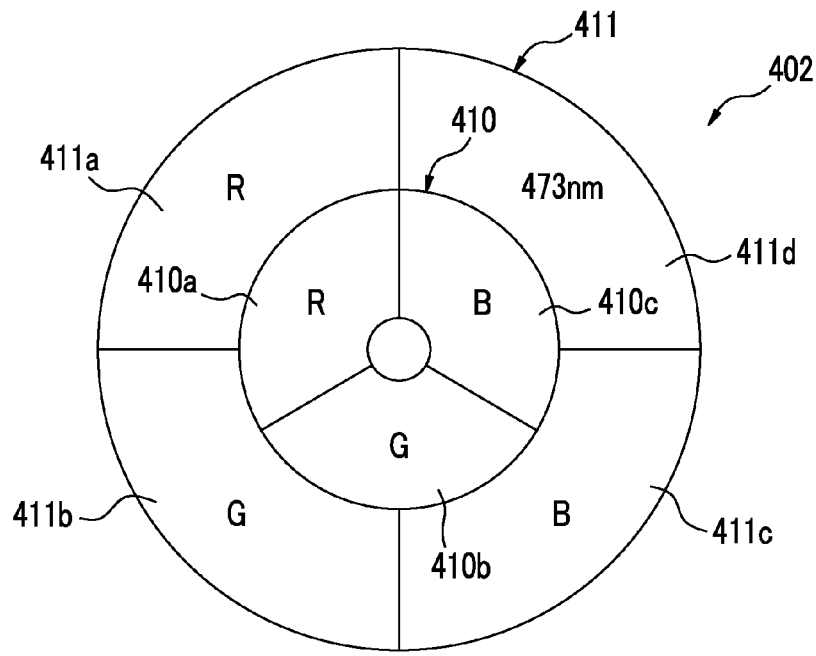
FIG. 29 is a plan view of a rotary filter.

As shown in FIG. 29, the normal observation mode filter 410 is provided in the inner peripheral portion of the rotary filter 402. The normal observation mode filter 410 includes an R filter 410a that transmits red light, a G filter 410b that transmits green light, and a B filter 410c that transmits blue light. Therefore, when the rotary filter 402 is placed at the first position for normal light observation mode, the white light from the broadband light source 401 is incident on one of the R filter 410a, the G filter 410b, and the B filter 410c according to the rotation of the rotary filter 402. As a result, red light, green light, and blue light are sequentially emitted to the observation target according to the transmitted filter, and the sensor 405 outputs sequentially an R image signal, a G image signal, and a B image signal by imaging the observation target with reflected light of the red light, the green light, and the blue light.

The special observation mode filter 411 is provided in the outer peripheral portion of the rotary filter 402. The special observation mode filter 411 includes an R filter 411a that transmits red light, a G filter 411b that transmits green light, a B filter 411c that transmits blue light, and a narrowband filter 411d that transmits narrowband light of 473±10 nm. Therefore, when the rotary filter 402 is placed at the second position for normal light observation mode, the white light from the broadband light source 401 is incident on one of the R filter 411a, the G filter 411b, the B filter 411c, and the narrowband filter 411d according to the rotation of the rotary filter 402. As a result, red light, green light, blue light, and narrowband light (473 nm) are sequentially emitted to the observation target according to the transmitted filter, and the sensor 405 outputs sequentially an R image signal, a G image signal, a B image signal, and a narrowband image signal by imaging the observation target with reflected light of the red light, the green light, the blue light, and the narrowband light.

The R image signal and the G image signal acquired in the special observation mode correspond to the R1 (or R2) image signal and the G1 (or G2) image signal in the first embodiment. The B image signal acquired in the special observation mode corresponds to the B2 image signal in the first embodiment, and the narrowband image signal corresponds to the B1 image signal. Accordingly, subsequent processing can be performed in the same manner as in the endoscope system 10 according to the first embodiment.

The broadband light source 401 and the rotary filter 402 form an illumination unit that generates illumination light that is emitted to the observation target. In the present embodiment, a series of light emitted to the observation target by using the special observation mode filter 411 is the first illumination light, and a series of light emitted to the observation target by using the normal observation mode filter 410 is the second illumination light.

Although the oxygen saturation is calculated based on the signal ratio B1/G2 and the signal ratio R2/G2 in the first to fourth embodiments, it is also possible to calculate the oxygen saturation based on only the signal ratio B1/G2. In this case, it is preferable to store the correlation between the signal ratio B1/G2 and the oxygen saturation in the correlation storage section 82.

Although the oxygen saturation image obtained by imaging the oxygen saturation is generated and displayed in the first to fourth embodiments, a blood volume image obtained by imaging the blood volume may be generated and displayed in addition to the generation and display of the oxygen saturation image. Since the blood volume is correlated with the signal ratio R2/G2, a blood volume image obtained by imaging the blood volume can be generated by assigning different colors according to the signal ratio R2/G2.

In the first to fourth embodiments, the oxygen saturation is calculated. However, instead of or in addition to the oxygen saturation, other biological function information, such as an oxygenated hemoglobin index that is calculated from "blood volume×oxygen saturation (%)" or a reduced hemoglobin index that is calculated from "blood volume× (1−oxygen saturation) (%)", may be calculated.

Figure 30:
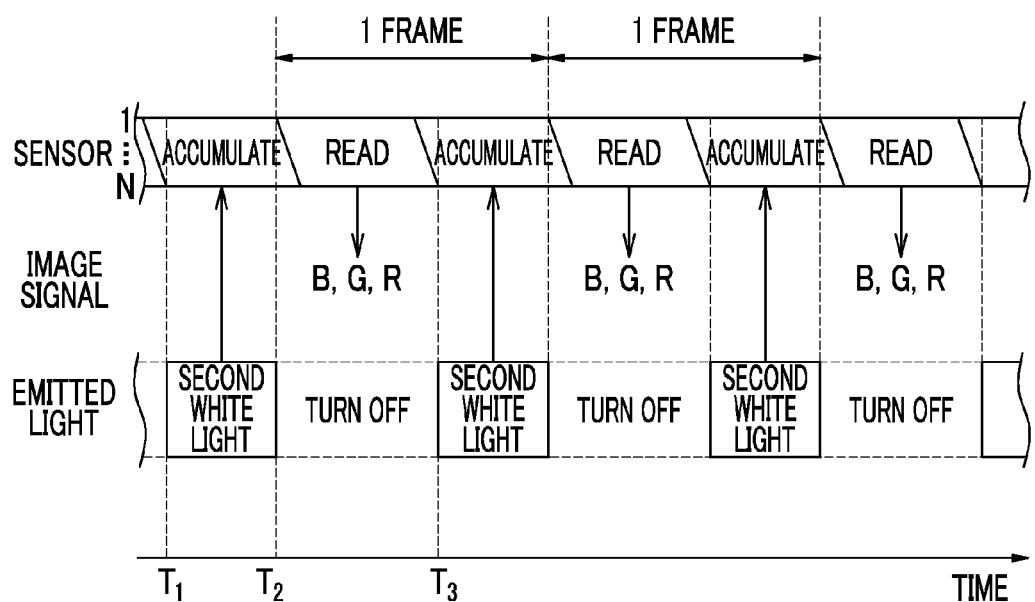
FIG. 30 is an explanatory view showing imaging control in the normal observation mode in the case of using a CMOS image sensor.
Figure 31:
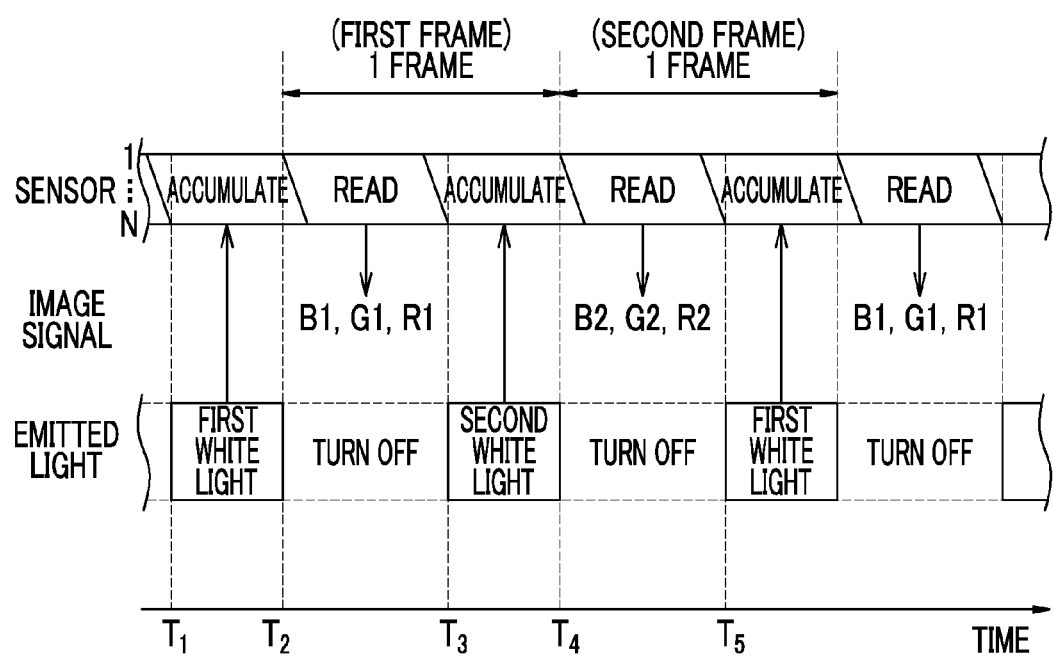
FIG. 31 is an explanatory view showing imaging control in the special observation mode in the case of using a CMOS image sensor.

Although the CCD image sensor is used as the sensor 48 in the first to fourth embodiments, a CMOS image sensor may also be used as the sensor 48. In this case, the CMOS image sensor is driven in a so-called rolling shutter method, and accumulation and reading of the signal charge are sequentially performed for each row (each of first to N-th rows) of pixels. For this reason, the timing of the accumulation and reading of the signal charge of each row differs according to each row. Therefore, switching between the first white light and the second white light is preferably performed in accordance with the reading timing. For example, as shown in FIG. 30, in the normal observation mode, the emission of the second white light is performed until the accumulation of the first row is completed (time $T_2$) from the start of the accumulation of the N-th row (time $T_1$), while the emission of the second white light is stopped until the reading of the N-th row is completed (time $T_3$) from the start of the reading of the first row (time $T_2$). In addition, as shown in FIG. 31, in the special observation mode, the emission of the second white light is performed until the accumulation of the first row is completed (time $T_2$) from the start of the accumulation of the N-th row (time $T_1$), while the emission of the second white light is stopped until the reading of the N-th row is completed (time $T_3$) from the start of the reading of the first row (time $T_2$). Then, in the next frame, the emission of the first white light is performed until the accumulation of the first row is completed (time $T_4$) from the start of the accumulation of the N-th row (time $T_3$), while the emission of the first white light is stopped until the reading of the N-th row is completed (time $T_5$) from the start of the reading of the first row (time $T_4$). Thus, it is possible to standardize the length (exposure) of the substantial charge accumulation period of each row and to prevent the signal based on the first white light and the signal based on the second white light from being mixed. Therefore, even when a CMOS image sensor is used as the sensor 48, it is possible to calculate an accurate oxygen saturation as in the embodiments described above. The same is true for a case when the LED light source unit 301 or the broadband light source 401 and the rotary filter 402 are used instead of the first and second blue laser light sources 34 and 36.

What is claimed is:

1. An endoscope system, comprising:
a light source device that generates illumination light to irradiate an observation target;
an endoscope that includes an imaging device that images the observation target with reflected light of the illumination light and that acquires a plurality of image signals from the imaging device, the plurality of image signals corresponding to a plurality of wavelength ranges including a wavelength range where an absorption coefficient changes according to oxygen saturation of blood hemoglobin; and
a processor device to:
calculate the oxygen saturation based on the image signals,
calculate an exposure amount designation value for designating an amount of exposure, which is required to image the observation target, based on the image signals,
calculate a threshold value for comparison with pixel values of the image signals according to the exposure amount designation value,
detect a first region, in which the pixel values fall within a range set by the threshold value, and a second region, in which the pixel values are out of the range, and
generate an oxygen saturation image, in which the oxygen saturation is displayed differently in the first and second regions, using the image signals, the oxygen saturation, and information of the first and second regions.

2. The endoscope system according to claim 1,
wherein the processor device increases the threshold value as the exposure amount designation value increases.

3. The endoscope system according to claim 2,
wherein the threshold value is one of a first threshold value used when the exposure amount designation value is larger than a first specific value, a second threshold value that is used when the exposure amount designation value is smaller than a second specific value set to be equal to or less than the first specific value and that is smaller than the first threshold value, and an intermediate value between the first and second threshold values that is used when the exposure amount designation value is equal to or greater than the second specific value and equal to or less than the first specific value.

4. The endoscope system according to claim 3,
wherein the intermediate value is a value that changes linearly with respect to the exposure amount designation value between the first and second threshold values.

5. The endoscope system according to claim 2,
wherein the processor device generates the oxygen saturation image in which one of the first and second regions is displayed in a color corresponding to a value of the oxygen saturation and the other region is displayed in a specific color that does not depend on the value of the oxygen saturation.

6. The endoscope system according to claim 5,
wherein the processor device displays the specific color by setting a color difference signal to zero in the generated oxygen saturation image.

7. The endoscope system according to claim 4,
wherein the processor device generates the oxygen saturation image in which one of the first and second regions is displayed in a color corresponding to a value of the oxygen saturation and the other region is displayed in a specific color that does not depend on the value of the oxygen saturation.

8. The endoscope system according to claim 7,
wherein the processor device displays the specific color by setting a color difference signal to zero in the generated oxygen saturation image.

9. The endoscope system according to claim 3,
wherein the processor device generates the oxygen saturation image in which one of the first and second regions is displayed in a color corresponding to a value of the oxygen saturation and the other region is displayed in a specific color that does not depend on the value of the oxygen saturation.

10. The endoscope system according to claim 9, wherein the processor device displays the specific color by setting a color difference signal to zero in the generated oxygen saturation image.

11. The endoscope system according to claim 1, wherein the processor device generates the oxygen saturation image in which one of the first and second regions is displayed in a color corresponding to a value of the oxygen saturation and the other region is displayed in a specific color that does not depend on the value of the oxygen saturation.

12. The endoscope system according to claim 11, wherein the processor device displays the specific color by setting a color difference signal to zero in the generated oxygen saturation image.

13. An endoscope system, comprising:
a light source device that generates illumination light to irradiate an observation target;
an endoscope that includes an imaging device that images the observation target with reflected light of the illumination light and that acquires a plurality of image signals from the imaging device, the plurality of image signals corresponding to a plurality of wavelength ranges including a wavelength range where an absorption coefficient changes according to oxygen saturation of blood hemoglobin;
a processor device to:
calculate the oxygen saturation based on the image signals,
calculate an exposure amount designation value for designating an amount of exposure, which is required to image the observation target, based on the image signals,
calculate a threshold value for comparison with a calculation value, which is calculated based on pixel values of the image signals, according to the exposure amount designation value,
calculate the calculation value based on the image signals and detects a first region, in which the calculation value falls within a range set by the threshold value, and a second region, in which the pixel values are out of the range, and
generate an oxygen saturation image, in which the oxygen saturation is displayed differently in the first and second regions, using the image signals, the oxygen saturation, and information of the first and second regions.

14. The endoscope system according to claim 13, wherein the calculation value is a ratio of a pixel value of each pixel to an average value of pixel values of all pixels of the image signals.

15. The endoscope system according to claim 13, wherein the calculation value is an average value of pixel values.

16. A processor device for an endoscope system which includes a light source device configured to generate illumination light to irradiate an observation target and an imaging device configured to image the observation target with reflected light of the illumination light and in which a plurality of image signals corresponding to a plurality of wavelength ranges including a wavelength range where an absorption coefficient changes according to oxygen saturation of blood hemoglobin are output from the imaging device, the endoscope system processor device comprising:

an endoscope that acquires the image signals; and
a processor device to:
calculate the oxygen saturation based on the image signals,
calculate an exposure amount designation value for designating an amount of exposure, which is required to image the observation target, based on the image signals,
calculate a threshold value for comparison with pixel values of the image signals according to the exposure amount designation value,
detect a first region, in which the pixel values fall within a range set by the threshold value, and a second region, in which the pixel values are out of the range, and
generate an oxygen saturation image, in which the oxygen saturation is displayed differently in the first and second regions, using the image signals, the oxygen saturation, and information of the first and second regions.

17. An operation method for an endoscope system, comprising:
a step of generating illumination light to irradiate an observation target by a light source device;
a step of acquiring a plurality of image signals from an imaging device by imaging the observation target with reflected light of the illumination light by the imaging device, the plurality of image signals corresponding to a plurality of wavelength ranges including a wavelength range where an absorption coefficient changes according to oxygen saturation of blood hemoglobin;
a step of calculating the oxygen saturation based on the image signals by a processor device;
a step of calculating an exposure amount designation value for designating an amount of exposure, which is required to image the observation target, based on the image signals by the processor device;
a step of calculating a threshold value for comparison with pixel values of the image signals according to the exposure amount designation value by the processor device;
a step of detecting a first region, in which the pixel values fall within a range set by the threshold value, and a second region, in which the pixel values are out of the range, by the processor device; and
a step of generating an oxygen saturation image, in which the oxygen saturation is displayed differently in the first and second regions, using the image signals, the oxygen saturation, and information of the first and second regions by the processor device.

18. An operation method for the processor device used in an endoscope system which includes a light source device configured to generate illumination light to irradiate an observation target and an imaging device configured to image the observation target with reflected light of the illumination light and in which a plurality of image signals corresponding to a plurality of wavelength ranges including a wavelength range where an absorption coefficient changes according to oxygen saturation of blood hemoglobin are output from the imaging device, the operation method comprising:
a step of acquiring the image signals by an endoscope;
a step of calculating the oxygen saturation based on the image signals by a processor device;
a step of calculating an exposure amount designation value for designating an amount of exposure, which is required to image the observation target, based on the image signals by the processor device;

a step of calculating a threshold value for comparison with pixel values of the image signals according to the exposure amount designation value by the processor device;

a step of detecting a first region, in which the pixel values fall within a range set by the threshold value, and a second region, in which the pixel values are out of the range, by the processor device; and a step of generating an oxygen saturation image, in which the oxygen saturation is displayed differently in the first and second regions, using the image signals, the oxygen saturation, and information of the first and second regions by the processor device.

* * * * *